United States Patent
Murray et al.

(10) Patent No.: US 12,377,193 B2
(45) Date of Patent: Aug. 5, 2025

(54) INDIRECT METHOD OF ARTICULAR TISSUE REPAIR

(71) Applicants: Children's Medical Center Corporation, Boston, MA (US); Rhode Island Hospital, Providence, RI (US)

(72) Inventors: Martha M. Murray, Sherborn, MA (US); Braden C. Fleming, East Greenwich, RI (US)

(73) Assignees: The Children's Medical Center Corporation, Boston, MA (US); Rhode Island Hospital, Providence, RI (US)

( * ) Notice: Subject to any disclaimer, the term of this patent is extended or adjusted under 35 U.S.C. 154(b) by 0 days.

(21) Appl. No.: 16/310,029

(22) PCT Filed: Jul. 6, 2017

(86) PCT No.: PCT/US2017/040865
§ 371 (c)(1),
(2) Date: Dec. 14, 2018

(87) PCT Pub. No.: WO2018/009637
PCT Pub. Date: Jan. 11, 2018

(65) Prior Publication Data
US 2019/0134269 A1     May 9, 2019

Related U.S. Application Data
(60) Provisional application No. 62/358,661, filed on Jul. 6, 2016.

(51) Int. Cl.
*A61F 2/08*     (2006.01)
*A61L 27/24*     (2006.01)
(Continued)

(52) U.S. Cl.
CPC .............. *A61L 27/386* (2013.01); *A61F 2/08* (2013.01); *A61L 27/24* (2013.01); *A61L 27/54* (2013.01);
(Continued)

(58) Field of Classification Search
CPC ........ A61F 2/08; A61F 2/0811; A61F 2/0063; A61B 17/04; A61B 17/0401; A61B 17/0482
See application file for complete search history.

(56) References Cited

U.S. PATENT DOCUMENTS

| | | | |
|---|---|---|---|
| 2,127,903 A | 5/1936 | Bowen | |
| 3,176,316 A | 4/1965 | Bodell | |

(Continued)

FOREIGN PATENT DOCUMENTS

| | | | |
|---|---|---|---|
| CN | 1988859 A | 6/2007 | |
| CN | 101332134 A | 12/2008 | |

(Continued)

OTHER PUBLICATIONS

Masur et al., Myofibroblasts differentiate from fibroblasts when plated at low density, Proc. Natl. Acad. Sci. USA, Apr. 1996, pp. 4219-4223, Cell Biology, vol. 93.

(Continued)

*Primary Examiner* — Alvin J Stewart
(74) *Attorney, Agent, or Firm* — Offit Kurman; Gregory A. Grissett

(57) ABSTRACT

Methods and devices for the repair of a torn or injured ligament or tendon are provided. The methods include the use of multiple scaffolds, e.g., beads. The multiple scaffolds may be positioned along a suture or other device such that they are moveable with respect to one another or the injured tissue.

32 Claims, 16 Drawing Sheets

(51) Int. Cl.
*A61L 27/38* (2006.01)
*A61L 27/54* (2006.01)
*A61F 2/00* (2006.01)
*A61L 27/58* (2006.01)

(52) U.S. Cl.
CPC ............ *A61F 2/0063* (2013.01); *A61L 27/58* (2013.01); *A61L 2430/10* (2013.01)

(56) References Cited

U.S. PATENT DOCUMENTS

| | | |
|---|---|---|
| 3,195,778 A | 7/1965 | Coates |
| 3,373,906 A | 3/1968 | DeHart et al. |
| 3,545,008 A * | 12/1970 | Bader, Jr. ............... A61F 2/08 623/13.15 |
| 3,587,982 A | 6/1971 | Campbell |
| 3,738,535 A | 6/1973 | Nicholls |
| 3,774,604 A | 11/1973 | Danielsson |
| 3,797,499 A | 3/1974 | Schneider |
| 3,805,300 A * | 4/1974 | Tascon-Alonso ........ A61F 2/08 623/13.14 |
| 3,893,834 A | 7/1975 | Armstrong |
| 4,069,814 A | 1/1978 | Clemens |
| 4,186,448 A | 2/1980 | Brekke |
| 4,187,558 A * | 2/1980 | Dahlen ................... A61F 2/08 623/13.14 |
| 4,255,820 A * | 3/1981 | Rothermel ............... A61F 2/08 623/13.11 |
| 4,265,618 A | 5/1981 | Herskovitz et al. |
| 4,326,540 A | 4/1982 | Bailey et al. |
| 4,400,833 A * | 8/1983 | Kurland ............ A61B 17/1146 623/1.32 |
| 4,455,690 A * | 6/1984 | Homsy ..................... A61F 2/08 623/13.15 |
| 4,458,678 A | 7/1984 | Yannas et al. |
| 4,467,806 A | 8/1984 | Bhiwandiwala et al. |
| 4,469,101 A * | 9/1984 | Coleman ............ A61B 17/1146 606/151 |
| 4,483,023 A * | 11/1984 | Hoffman, Jr. ............ A61F 2/08 623/13.15 |
| 4,578,067 A | 3/1986 | Cruz, Jr. |
| 4,584,722 A * | 4/1986 | Levy ........................ A61F 2/08 623/13.15 |
| 4,585,458 A | 4/1986 | Kurland |
| 4,610,688 A * | 9/1986 | Silvestrini ............. A61F 2/2412 623/1.53 |
| 4,642,119 A * | 2/1987 | Shah ........................ A61F 2/08 623/13.2 |
| 4,662,886 A * | 5/1987 | Moorse ................... A61L 27/08 623/13.15 |
| 4,713,075 A * | 12/1987 | Kurland ............ A61B 17/1146 128/898 |
| 4,731,084 A * | 3/1988 | Dunn ....................... A61F 2/08 623/13.19 |
| 4,753,536 A | 6/1988 | Spehar et al. |
| 4,775,380 A * | 10/1988 | Seedhom ............... A61B 17/88 623/13.16 |
| 4,808,184 A | 2/1989 | Tepic |
| 4,808,570 A | 2/1989 | Michaeli |
| 4,846,835 A | 7/1989 | Grande |
| 4,851,513 A | 7/1989 | Devore et al. |
| 4,883,486 A * | 11/1989 | Kapadia ................... A61F 2/08 623/13.15 |
| 4,894,063 A * | 1/1990 | Nashef ................. A61F 2/0077 623/13.17 |
| 4,917,699 A * | 4/1990 | Chervitz ................... A61F 2/08 623/13.19 |
| 4,917,700 A * | 4/1990 | Aikins ..................... A61F 2/08 623/13.19 |
| 4,932,942 A | 6/1990 | Maslanka |
| 4,944,755 A * | 7/1990 | Hennequin ............... A61F 2/08 623/18.11 |
| 4,946,377 A * | 8/1990 | Kovach ................... A61F 2/08 623/13.18 |
| 4,955,893 A | 9/1990 | Yannas et al. |
| 4,959,058 A | 9/1990 | Michelson |
| 4,973,321 A | 11/1990 | Michelson |
| 5,007,934 A | 4/1991 | Stone |
| 5,037,396 A | 8/1991 | Streeter |
| 5,078,744 A | 1/1992 | Chvpil |
| 5,078,745 A * | 1/1992 | Rhenter ................... A61F 2/08 623/13.12 |
| 5,119,669 A | 6/1992 | Silvis et al. |
| 5,152,462 A | 10/1992 | Evans |
| 5,171,273 A | 12/1992 | Silver et al. |
| 5,171,274 A * | 12/1992 | Fluckiger ................ A61F 2/08 623/13.16 |
| 5,176,708 A * | 1/1993 | Frey .......................... A61F 2/08 623/13.2 |
| 5,197,983 A * | 3/1993 | Berman ................... A61F 2/08 623/13.2 |
| 5,206,023 A | 4/1993 | Hunziker |
| 5,206,028 A | 4/1993 | Li |
| 5,217,495 A * | 6/1993 | Kaplan ..................... A61F 2/06 57/225 |
| 5,275,826 A | 1/1994 | Badylak et al. |
| 5,281,422 A | 1/1994 | Badylak et al. |
| 5,306,301 A | 4/1994 | Graf et al. |
| 5,370,662 A | 12/1994 | Stone et al. |
| 5,376,118 A * | 12/1994 | Kaplan ..................... A61F 2/06 606/228 |
| 5,380,087 A | 1/1995 | Haber et al. |
| 5,436,135 A | 7/1995 | Tayot et al. |
| 5,445,833 A | 8/1995 | Badylak et al. |
| 5,455,833 A | 10/1995 | Herre et al. |
| 5,456,721 A * | 10/1995 | Legrand ................... A61F 2/08 623/1.5 |
| 5,458,636 A * | 10/1995 | Brancato ............... A61F 2/0063 623/23.72 |
| 5,467,786 A | 11/1995 | Allen et al. |
| 5,474,450 A | 12/1995 | Chronister |
| 5,503,616 A | 4/1996 | Jones |
| 5,522,840 A | 6/1996 | Krajicek |
| 5,549,676 A * | 8/1996 | Johnson ................... A61F 2/08 623/13.13 |
| 5,556,429 A | 9/1996 | Felt |
| 5,595,621 A | 1/1997 | Light et al. |
| 5,652,077 A | 7/1997 | Obinata |
| 5,655,546 A | 8/1997 | Halpern |
| 5,681,353 A | 10/1997 | Li et al. |
| 5,688,276 A | 11/1997 | Shaffer |
| 5,713,374 A | 2/1998 | Pachence et al. |
| 5,749,895 A | 5/1998 | Sawyer et al. |
| 5,756,127 A | 5/1998 | Grisoni et al. |
| 5,800,543 A * | 9/1998 | McLeod ................... A61F 2/08 623/13.2 |
| 5,810,884 A | 9/1998 | Kim |
| 5,855,619 A * | 1/1999 | Caplan ............... A61B 17/1146 623/23.72 |
| 5,897,591 A | 4/1999 | Kobayashi |
| 5,902,741 A | 5/1999 | Purchio et al. |
| 5,968,018 A | 10/1999 | Freeman et al. |
| RE36,370 E | 11/1999 | Li |
| 5,993,844 A | 11/1999 | Abraham et al. |
| 6,007,580 A * | 12/1999 | Lehto ..................... A61F 2/4241 623/21.11 |
| 6,045,549 A | 4/2000 | Smethers et al. |
| 6,045,569 A | 4/2000 | Kensey et al. |
| 6,080,192 A | 6/2000 | Demopulos et al. |
| 6,087,113 A | 7/2000 | Caplan et al. |
| 6,096,309 A | 8/2000 | Prior et al. |
| 6,117,425 A | 9/2000 | MacPhee et al. |
| 6,129,757 A | 10/2000 | Weadock |
| 6,139,520 A | 10/2000 | McCrory et al. |
| 6,143,029 A * | 11/2000 | Rippstein ................ A61F 2/08 602/36 |
| 6,153,292 A | 11/2000 | Bell et al. |
| 6,171,610 B1 | 1/2001 | Vacanti et al. |
| 6,174,333 B1 | 1/2001 | Kadiyala et al. |
| 6,176,880 B1 | 1/2001 | Plouhar et al. |
| 6,203,572 B1 * | 3/2001 | Johnson ................... A61F 2/08 606/108 |

(56) References Cited

U.S. PATENT DOCUMENTS

| | | | |
|---|---|---|---|
| 6,214,047 B1* | 4/2001 | Melvin | A61F 2/08 623/11.11 |
| 6,214,049 B1 | 4/2001 | Garyer et al. | |
| 6,234,795 B1 | 5/2001 | Fischer | |
| 6,280,474 B1 | 8/2001 | Cassidy et al. | |
| 6,283,996 B1 | 9/2001 | Chervitz et al. | |
| 6,309,372 B1 | 10/2001 | Fischer et al. | |
| 6,365,149 B2 | 4/2002 | Vyakarnam et al. | |
| 6,398,761 B1 | 6/2002 | Bills et al. | |
| 6,454,129 B1 | 9/2002 | Green | |
| 6,472,210 B1 | 10/2002 | Holy et al. | |
| 6,517,578 B2* | 2/2003 | Hein | A61F 2/0811 606/232 |
| 6,592,623 B1* | 7/2003 | Bowlin | A61F 2/08 623/13.17 |
| 6,629,997 B2 | 10/2003 | Mansmann | |
| 6,689,153 B1 | 2/2004 | Skiba | |
| 6,699,214 B2 | 3/2004 | Gellman | |
| 6,946,003 B1 | 9/2005 | Wolowacz et al. | |
| 6,964,685 B2 | 11/2005 | Murray et al. | |
| 6,971,787 B2 | 12/2005 | Botrie et al. | |
| 6,989,034 B2 | 1/2006 | Hammer et al. | |
| 7,119,062 B1 | 10/2006 | Alvis et al. | |
| 7,148,209 B2 | 12/2006 | Hoemann et al. | |
| 7,156,880 B2 | 1/2007 | Evans et al. | |
| 7,250,057 B2 | 7/2007 | Forsberg | |
| 7,335,220 B2 | 2/2008 | Khosravi et al. | |
| 7,652,077 B2 | 1/2010 | Cook et al. | |
| 7,838,630 B2 | 11/2010 | Murray et al. | |
| 7,901,461 B2 | 3/2011 | Harmon et al. | |
| 8,002,813 B2 | 8/2011 | Scarborough et al. | |
| 8,070,827 B2 | 12/2011 | Shortkroff et al. | |
| 8,137,686 B2 | 3/2012 | Kladakis et al. | |
| 8,308,681 B2 | 11/2012 | Slocum et al. | |
| 8,642,735 B2 | 2/2014 | Murray et al. | |
| 8,652,171 B2* | 2/2014 | Stone | A61B 17/0401 606/232 |
| 9,308,242 B2 | 4/2016 | Murray | |
| 9,314,241 B2* | 4/2016 | Stone | A61B 17/0401 |
| 9,414,833 B2* | 8/2016 | Stone | A61B 17/0482 |
| 9,757,495 B2 | 9/2017 | Murray | |
| 9,849,213 B2 | 12/2017 | Murray | |
| 9,867,902 B2* | 1/2018 | Giraud-Guille | A61L 27/24 |
| 9,918,826 B2* | 3/2018 | Berelsman | A61B 17/06166 |
| 9,918,827 B2* | 3/2018 | Berelsman | A61B 17/0401 |
| 9,955,980 B2* | 5/2018 | Norton | A61B 17/1604 |
| 10,092,288 B2* | 10/2018 | Denham | A61B 17/06166 |
| 10,136,886 B2* | 11/2018 | Norton | A61B 17/0487 |
| 10,675,016 B2* | 6/2020 | Coleman | A61B 17/04 |
| 10,675,141 B2* | 6/2020 | Greenhalgh | A61F 2/08 |
| 10,702,260 B2* | 7/2020 | Sengun | A61F 2/0811 |
| 10,729,430 B2* | 8/2020 | Denham | A61B 17/0401 |
| 10,758,644 B2* | 9/2020 | Derwin | A61P 21/00 |
| 10,786,232 B2 | 9/2020 | Murray | |
| 10,786,238 B2* | 9/2020 | Murray | A61B 17/1146 |
| 10,835,235 B2* | 11/2020 | Coleman | A61F 2/0063 |
| 10,842,914 B2 | 11/2020 | Murray | |
| 11,076,845 B2 | 8/2021 | Murray | |
| 11,076,846 B2 | 8/2021 | Murray | |
| 11,484,578 B2 | 11/2022 | Murray et al. | |
| 2001/0044659 A1* | 11/2001 | Laboureau | A61F 2/08 623/13.2 |
| 2002/0022884 A1 | 2/2002 | Mansmann | |
| 2002/0038151 A1* | 3/2002 | Plouhar | A61L 27/3629 623/23.72 |
| 2002/0055749 A1* | 5/2002 | Esnouf | A61F 2/08 606/148 |
| 2002/0123805 A1 | 9/2002 | Murray et al. | |
| 2002/0161450 A1 | 10/2002 | Doi et al. | |
| 2002/0183845 A1 | 12/2002 | Mansmann et al. | |
| 2003/0012805 A1 | 1/2003 | Chen et al. | |
| 2003/0023316 A1* | 1/2003 | Brown | A61L 27/3641 623/23.72 |
| 2003/0033022 A1* | 2/2003 | Plouhar | A61F 2/08 623/23.57 |
| 2003/0078659 A1 | 4/2003 | Yang | |
| 2003/0147935 A1 | 8/2003 | Binette et al. | |
| 2003/0163144 A1 | 8/2003 | Weadock et al. | |
| 2003/0167053 A1 | 9/2003 | Taufig | |
| 2003/0212456 A1* | 11/2003 | Lipchitz | A61F 2/08 623/13.17 |
| 2003/0236573 A1 | 12/2003 | Evans et al. | |
| 2004/0005297 A1 | 1/2004 | Connelly et al. | |
| 2004/0024456 A1* | 2/2004 | Brown, Jr. | A61B 17/3431 623/13.15 |
| 2004/0059416 A1 | 3/2004 | Murray et al. | |
| 2004/0078077 A1 | 4/2004 | Binette et al. | |
| 2004/0170664 A1 | 9/2004 | Spector et al. | |
| 2004/0243235 A1 | 12/2004 | Goh et al. | |
| 2004/0258729 A1 | 12/2004 | Czernuszka et al. | |
| 2004/0262332 A1 | 12/2004 | Pauser et al. | |
| 2004/0267362 A1* | 12/2004 | Hwang | A61F 2/08 623/13.15 |
| 2005/0027307 A1 | 2/2005 | Schwartz et al. | |
| 2005/0100536 A1 | 5/2005 | Mishra | |
| 2005/0129730 A1 | 6/2005 | Pang et al. | |
| 2005/0183731 A1 | 8/2005 | Hunter et al. | |
| 2005/0192581 A1* | 9/2005 | Molz | D04C 1/12 606/74 |
| 2005/0230422 A1 | 10/2005 | Muller et al. | |
| 2005/0025514 A1 | 11/2005 | Hagan et al. | |
| 2005/0261736 A1 | 11/2005 | Murray et al. | |
| 2005/0267521 A1 | 12/2005 | Forsberg | |
| 2006/0190041 A1 | 8/2006 | Fallin et al. | |
| 2007/0118217 A1* | 5/2007 | Brulez | A61F 2/08 623/13.2 |
| 2007/0150064 A1* | 6/2007 | Ruberte | A61F 2/442 623/17.16 |
| 2007/0269476 A1 | 11/2007 | Voytik-Harbin et al. | |
| 2007/0288023 A1* | 12/2007 | Pellegrino | A61B 17/0401 606/232 |
| 2008/0027542 A1* | 1/2008 | McQuillan | A61L 27/3662 623/13.11 |
| 2008/0097430 A1* | 4/2008 | Bernstein | A61B 17/1796 606/60 |
| 2008/0188936 A1* | 8/2008 | Ball | A61B 17/1146 623/13.14 |
| 2008/0195205 A1 | 8/2008 | Schwartz | |
| 2008/0228271 A1* | 9/2008 | Stone | A61F 2/0811 623/13.12 |
| 2009/0018655 A1* | 1/2009 | Brunelle | A61L 27/24 623/13.19 |
| 2009/0143765 A1 | 6/2009 | Slocum et al. | |
| 2009/0171143 A1* | 7/2009 | Chu | A61B 17/06109 600/37 |
| 2009/0254104 A1 | 10/2009 | Murray | |
| 2009/0306776 A1* | 12/2009 | Murray | A61L 27/24 623/13.12 |
| 2010/0106254 A1* | 4/2010 | DelSignore | A61F 2/0811 623/21.15 |
| 2010/0221835 A1 | 9/2010 | Tanaka et al. | |
| 2010/0298937 A1* | 11/2010 | Laurencin | A61L 27/14 623/13.14 |
| 2011/0027338 A1 | 2/2011 | Murray et al. | |
| 2011/0054524 A1* | 3/2011 | Beevers | A61F 2/0811 606/228 |
| 2011/0184227 A1* | 7/2011 | Altman | A61F 2/12 600/37 |
| 2011/0295284 A1* | 12/2011 | Purdue | A61F 2/08 606/151 |
| 2011/0306555 A1 | 12/2011 | Murray et al. | |
| 2012/0071975 A1* | 3/2012 | Gonzalez-Hernandez | A61B 17/1146 623/13.11 |
| 2012/0123474 A1 | 5/2012 | Zajac et al. | |
| 2012/0201896 A1 | 8/2012 | Murray et al. | |
| 2012/0226296 A1* | 9/2012 | Bindra | A61B 17/1146 606/151 |
| 2012/0283831 A1 | 11/2012 | Murray | |

(56) References Cited

U.S. PATENT DOCUMENTS

| | | | |
|---|---|---|---|
| 2013/0142840 A1* | 6/2013 | Giraud-Guille | A61L 27/24 514/17.2 |
| 2013/0231609 A1 | 9/2013 | Slocum et al. | |
| 2013/0273017 A1 | 10/2013 | Murray | |
| 2013/0345810 A1* | 12/2013 | Jaeger | A61F 2/0045 623/13.11 |
| 2014/0039620 A1* | 2/2014 | Cantournet | A61F 2/08 623/13.14 |
| 2014/0134249 A1 | 5/2014 | Murray et al. | |
| 2014/0172096 A1* | 6/2014 | Koob | D04C 1/12 623/13.19 |
| 2014/0369984 A1 | 12/2014 | Murray et al. | |
| 2015/0088198 A1 | 3/2015 | Spenciner et al. | |
| 2015/0359530 A1* | 12/2015 | Moore | A61F 2/0811 606/232 |
| 2015/0367030 A1 | 12/2015 | Murray | |
| 2016/0081790 A1 | 3/2016 | Cournoyer et al. | |
| 2016/0206779 A1 | 7/2016 | Murray | |
| 2016/0263279 A1 | 9/2016 | Murray et al. | |
| 2016/0354195 A1* | 12/2016 | Spenciner | A61F 2/08 |
| 2017/0143551 A1* | 5/2017 | Coleman | A61B 17/00 |
| 2017/0156727 A1* | 6/2017 | Wilson-Wirth | A61L 17/105 |
| 2017/0232144 A1* | 8/2017 | Kelly | A61L 27/3654 424/423 |
| 2017/0273775 A1* | 9/2017 | Rocco | A61F 2/0077 |
| 2017/0281327 A1* | 10/2017 | Kaplan | A61F 2/08 |
| 2017/0340772 A1 | 11/2017 | Murray | |
| 2017/0360437 A1* | 12/2017 | Ferguson | A61B 17/0401 |
| 2017/0360986 A1* | 12/2017 | Paten | A61K 38/4886 |
| 2018/0207316 A1 | 7/2018 | Murray | |
| 2018/0228598 A1* | 8/2018 | Mathisen | A61L 27/56 |
| 2019/0134269 A1 | 5/2019 | Murray et al. | |
| 2019/0380693 A1* | 12/2019 | Burkhart | A61B 17/0401 |
| 2019/0388582 A1 | 12/2019 | Murray | |
| 2020/0000573 A1* | 1/2020 | Whittaker | A61B 17/0483 |
| 2020/0009292 A1 | 1/2020 | Murray | |
| 2020/0171203 A1 | 6/2020 | Murray | |
| 2020/0196998 A1 | 6/2020 | Murray | |
| 2020/0196999 A1 | 6/2020 | Murray | |
| 2020/0214690 A1 | 7/2020 | Murray | |
| 2020/0222586 A1 | 7/2020 | Murray | |
| 2020/0253715 A1* | 8/2020 | Trenhaile | A61F 2/0811 |
| 2020/0345475 A1* | 11/2020 | Lima | D02G 3/36 |
| 2022/0096710 A1 | 3/2022 | Murray | |

FOREIGN PATENT DOCUMENTS

| | | |
|---|---|---|
| CN | 102488713 A | 6/2012 |
| CN | 104939877 A | 9/2015 |
| CN | 105007846 A | 10/2015 |
| CN | 105120774 A | 12/2015 |
| CN | 105125272 A | 12/2015 |
| CN | 105142540 A | 12/2015 |
| CN | 105208970 A | 12/2015 |
| CN | 105214141 A | 1/2016 |
| CN | 105250049 A | 1/2016 |
| EP | 0295721 A2 | 12/1988 |
| EP | 0445951 A2 | 9/1991 |
| EP | 0645149 A1 | 3/1995 |
| EP | 1254671 A1 | 11/2002 |
| EP | 1273312 A1 | 1/2003 |
| EP | 3798226 A1 | 3/2021 |
| EP | 4162936 A1 | 4/2023 |
| GB | 2106794 A | 4/1983 |
| WO | 8500511 A1 | 2/1985 |
| WO | 9213565 A1 | 8/1992 |
| WO | 9311723 A1 | 6/1993 |
| WO | 9321857 A1 | 11/1993 |
| WO | 9525550 A1 | 9/1995 |
| WO | 9940771 A1 | 8/1999 |
| WO | 2000047130 A1 | 8/2000 |
| WO | 2000074760 A2 | 12/2000 |
| WO | 2001066130 A1 | 9/2001 |
| WO | 2002067812 A2 | 9/2002 |
| WO | 2003011107 A2 | 2/2003 |
| WO | 2003105737 A1 | 12/2003 |
| WO | 2004078134 A2 | 9/2004 |
| WO | 2006086479 A2 | 8/2006 |
| WO | 2007087353 A2 | 8/2007 |
| WO | 2008036393 A1 | 3/2008 |
| WO | 2008060361 A2 | 5/2008 |
| WO | 2008109407 A2 | 9/2008 |
| WO | 2008109807 A2 | 9/2008 |
| WO | 2010048418 A1 | 4/2010 |
| WO | 2010084481 A1 | 7/2010 |
| WO | 2010108237 A1 | 9/2010 |
| WO | 2013116744 A1 | 8/2013 |
| WO | 2014121067 A1 | 8/2014 |
| WO | 2014137557 A1 | 9/2014 |
| WO | 2014138467 A1 | 9/2014 |
| WO | 2014151766 A1 | 9/2014 |
| WO | 2014165036 A1 | 10/2014 |
| WO | 2018009634 A1 | 1/2018 |

OTHER PUBLICATIONS

Murray et al., Migration of Human Anterior Cruciate Ligament Fibrosis Into Porous Collagen-GAG Matrices In Vitro, 24th Annual Meeting of the Society for Biomaterials, San Diego, CA, Apr. 22-26, 1996, pp. 463.

Murray et al., The Migration of Human Anterior Cruciate Ligament Fibroblasts Into Porous Collagen-GAG Matrices In Vitro, 45th Annual Meeting, Orthopaedic Research Society, Anaheim, CA, Feb. 1-4, 1999, 1 pp.

Murray et al., Differences in the Outgrowth of Cells from Explants from the Proximal and Distal Human ACL and Responses to TGF-B1, 47th Annual Meeting, Orthopaedic Research Society, San Francisco, CA, Feb. 25-28, 2001, pp. 0788.

Murray et al., The Effects of Selected Growth Factors on Human ACL Cell Interactions with 3-D Collagen-GAG Scaffolds, 47th Annual Meeting, Orthodaedic Research Society, San Francisco, CA, Feb. 25-28, 2001, pp. 0790.

Murray et al., The migration of cells from the ruptured human anterior cruciate ligament into collagen-glycosaminoglycan regeneration templates in vitro, Biomaterials 22, 2001 Elsevier, pp. 2393-2402.

Murray et al., The Effect Ruptured Human Anterior Cruciate Ligament Histology on Cell Interactions with a Collagen-GAG Scaffold In Vitro, Davos Tissue Engineering Workshop, Davos Switzerland, 2000, I pp.

Murray et al., Histological Changes in the Human Anterior Cruciate Ligament After Rupture, The Journal of Bone and Joint Surgery Incorporated, Oct. 2000, pp. 1387-1397, vol. 82-A, No. 10.

Murray et al., Fibroblast Distribution in the Anteromedial Bundle of the Human Anterior Cruciate Ligament: The Presence of alpha smooth muscle actin-positive cells, J. Orthop. Res., 1999, pp. 18-27, vol. 17., No. 1.

Murray et al., Migration os Cells from Human Anterior Cruciate Ligament Explants into Collagen-Glycosaminoglycan Scaffolds, Journal of Orthopaedic Research, 2000., pp. 557-564, vol. 18, No. 4.

Murray et al., Migration of Cells fro mRuptured Human Anterior Curciate Ligament Explants Into Collagen-GAG Matrices, 6th World Biomatrials Conference, Kamuela, HI, 2000, 1 pp.

Murray et al., Use of a Collagen-Platelet Rich Plasma Scaffold to Stimulate Healing of a Central Defect in the Canine ACL, Journal of Orthopaedic Research, Apr. 2006, pp. 820-830, Wilet InterScience.

Nakamura et al., A Comparison of in vivo gene delivery methods for antisense therapy in ligament healing, Gene Therapy, 1998, pp. 1455-1461, vol. 5.

Nakamura et al., Early biological effect of in vivo gene transfer of platelet-derived growth factor (PDGF)-B into healing patellar ligament, Gene Therapy, 1998, pp. 1165-1170, vol. 5.

Neuman et al. The Determination of Hydroxyproline, J. Biol. Chem, 184, 1950, pp. 299-306.

Niklason et al., Functional arteries grown in vitro, Copyright American Association for the Advancement of Science, Washington, Apr. 16, 1999, 6 pp.

(56) References Cited

OTHER PUBLICATIONS

[No Author Listed], Guidance Document for Testing Biodegradable Polymer Implant Devices, ODE Guidance Documents, Apr. 20, 1996, 11 pp.

[No Author Listed], Meriam Webster Dictionary, Definition carbonate-apatite, 7 pp, Date: Jan. 5, 2019.

Noyes et al., Bone-Patellar Ligament-Bone and Fascia Lata Allografts for Reconstruction of the Anterior Cruciate Ligament, The Journal of Bone and Joint Surgery, 1990, pp. 1125-1136, vol. 72-A, No. 8.

Officer Anita Meacle, European Office Action, European Patent Application No. 07 867 174.0, Nov. 29, 2018, 5 pp.

Parkhurst et al., Quantification of human neutrophil motility in three-dimensional collagen gels, Effect of collagen concentration, Biophys J, Biophysical Society, Feb. 1992, pp. 306-315, vol. 61.

Peter et al., Synthesis of poly (propylene fumarate) by acylation of propylebe glycol in the presence of a proton scavenger, Journal of Biomaterial Science, Polymer Edition, 1999, pp. 363-373, vol. 10, No. 3.

Qui et al. Outgrowth of chondrocytes from human articular cartilage explants and ecpression of alpha-smooth muscle actin, Wound Repair an d Regeneration, Sep.-Oct. 2000, pp. 383-391, vol. 8, No. 5.

Sadowska et al., Isolation of collagen from the skins of Baltic cod (*Gadus morhua*), Food Chemistry, 2003, pp. 257-262, Elsevier Science, Ltd.

Schmidt et al., Effect of Growth Factors on the Proliferation of Fibroblasts from the Medical Collateral and Anterior Cruciate Ligaments, Journal of Orthopaedic Research, The Journal of Bone and Joint Surgert, Inc., 1995, pp. 184-190, vol. 13, No. 2.

Schulz Torres et al., Effects of Modulus of Elasticity of Collagen Sponges on Their Cell-Medicated Contraction In Vitro, Massachusetts Institute of Technology, Jun. 1998, 96 pp.

Spindler et al., Comparison of Collagen Synthesis in the Peripheral and Central Region of the Canine Meniscus, Clinical Orthopaedics, Jun. 1994, pp. 256-263, vol. 303.

Spindler et al., Regional Mitogenic Response of the Meniscus to Platelet-Derived Growth Factor (PDGF-AB), Journal of Orthopaedic Research, The Journal od Bone and Joint Surgery, Inc., 1995, pp. 201-207, vol. 13, No. 2.

Spindler et al., Patellar Tendon and Anterior Cruciate Ligament Have Different Mitogenic Responses to Platelet-Derived Growth Factor and Transforming Growth Factor Beta, Journal of Orthpaedic Research, The Journal of Bone and Joint Surgery, Inc., 1996, pp. 542-546, vol. 14, No. 4.

Stensel et al., Collagen as a Biomaterial, Annual Review Biophysics Bioenginering, 1974, 24 pp.

Stevenson et al., Gender Differences in Knee Injury Epidemiology Among Competitive Alpine Ski Racers, The Iowa Orthopaedic Journal, 1998, pp. 64-66, vol. 18.

Stone et al., Future Directions Collagen-Based Prostases for Meniscal Regeneration, Clinical Orthopaedics and Related Research, Mar. 1990, pp. 129-136, No. 252.

Stone et al., Regeneration of Meniscal Cartilage with Use of a Collagen Scaffold, The Journal of Bone and Joint Surgery, Incorporated, Dec. 1997, pp. 1770-1777, vol. 79-A, No. 12.

Suggs et al., Platelet adhesion on a bioresorbable poly (propylene fumarate-co-ethylene glycol) copolymer, Biomaterials 20, 1999, pp. 683-690, Elsevier Science Ltd.

Troxel, Karen S., Delay of Skin Would Contraction by Porous Collagen-GAG Matrices, (Ph.D. Thesis, Massachusetts Institute of Technology), 1994, 1 pp.

Weadock et al., Physical crosslinking of collagen fibers: Comparison of ultraviolet irradiation and dehydrothermal treatment, Journal of Biomedical Materials Research, 1995, pp. 1373-1379, vol. 29.

Witkowski et al., Migration and Healing of Ligament Cells under Inflammatory Conditions, Journal of Orthopaedic Research, The Journal of Bone and Joint Surgery, Inc., 1997, pp. 269-277, vol. 15, No. 2.

Yannas, Ioannis V., Models of Organ Regeneration Processes Induced by Templates, Bioartificial Organs: Science, Medicine and Technology, 1997, pp. 280-293, The New York Academy of Sciences, New York, NY.

Yannas, Ioannis V., Regeneration of Skin and Nerve by Use of Collagen Templates, Collagen, Sep. 23, 2002, pp. 87-115, vol. III, No. 3345.

Yannas et al., Polymeric Template Facilitates Regeneration of Sciatic Nerve Across, The 11th Annual Meeting of the Society for Biomaterials, San Diego, CA, Apr. 25-28, 1985, pp. 146.

Yannas et al., Synthesis and characterization of a model extracellular matrix that induces partial regeneration of adult mammalian skin, Developmental Biology, Proc. Nat'l. Acad. Sci. USA, Feb. 1989. pp. 933-937, vol. 86, No. 3.

Al-Munajjed et al., Development of a collagen calcium-phosphate scaffold as a novel bone graft substitute, Royal College of Surgeons in Ireland, Jan. 1, 2008, 10 pp.

Anseth et al., Photopolymerizable degradable polyanhydrides with osteocompatibility, Nature Biotechnology, Feb. 1999, pp. 156-159, vol. 17.

Arendt et al., Knee Injury Patterns Among Men and Women in Collegiate Basketball and Soccer, The American Journal of Sports Medicine, American Orthopaedic Society for Sports Medicine, 1995, pp. 694-701, Vo. 23, No. 6.

Authorized Officer Athina Nickitas-Etienne, International Preliminary Report on Patentability, International Patent Application No. PCT/US2014/014141, May 13, 2014, 9 pp.

Authorized Officer Athina Nickitas-Etienne, International Preliminary Report on Patentability, International Patent Application No. PCT/US2006/004445, Feb. 17, 2009, 4 pp.

Authorized Officer Aurore Schneider, International Search Report and the Written Opinion, International Patent Application No. PCT/US2017/040865, Oct. 19, 2017, 8 pp.

Authorized Officer Brian Pellegrino, International Search Report, International Patent Application PCT/US2002/023885, Sep. 30, 2002, 3 pp.

Authorized Officer Brian Pellegrino, International Preliminary Examination Report, International Patent Application PCT/US2002/023885, Jan. 30, 2003, 3 pp.

Authorized Officer Ellen Moyse, International Preliminary Report on Patentability, International Patent Application No. PCT/US2007/001908, Jul. 29, 2008, 9 pp.

Authorized Officer Ellen Moyse, International Preliminary Report on Patentability, International Patent Application No. PCT/US2007/021009, Jan. 12, 2010, 13 pp.

Authorized Officer Lee W. Wong, International Search Report and the Written Opinion, International Patent Application No. PCT/US2007/001908, Sep. 5, 2007, 10 pp.

Authorized Officer Manuel A. Mendez, International Search Report and the Written Opinion, International Patent Application No. PCT/US2006/004445, Jun. 13, 2008, 5 pp.

Authorized Officer Monica Lopez Garcia, International Search Report and the Written Opinion, International Patent Application No. PCT/US2007/021009, Sep. 1, 2009, 18 pp.

Authorized Officer Ross Heosey, International Search Report and the Written Opinion, International Patent Application No. PCT/US2013/024467, Apr. 29, 2013, 12 pp.

Authorized Officer Shawn Lyons, International Search Report and the Written Opinion, International Patent Application No. PCT/US2014/014141, May 13, 2014, 14 pp.

Authorized Officer Simin Baharlou, International Preliminary Report on Patentability, International Patent Application No. PCT/US2017/040865, Jan. 8, 2019, 6 pp.

Buck, R.C., Regeneration of Tendon, The Journal of Pathology and Bacteriology, 1953, 22 pp., vol. LXVI, No. I.

Chamberlain et al., Early peripheral nerve healing in collagen and silicone tube implants: Myofibroblasts and the cellular response, Biomaterials 19, Elsevier, 1998, pp. 1393-1403.

Chamberlain et al., Collagen-GAG Substrate Enhances the Quality of Nerve Regeneration through Collagen Tubes up to Level of Autograft, Experimental Neurology 154, 1998, pp. 315-329, American Press.

(56) References Cited

OTHER PUBLICATIONS

Chamberlain, Lila Jo, Long Term Functional and Morphological Evaluation of Peripheral Nerves Regenerated Through Degradable Collagen Implants, MS Thesis, Massachusetts Institute of Technology, 1998, pp. 2.
Crapo et al., An overview of tissue and whole organ decellularization processes, NIH Public Access, Elsevier, Ltd., Biomaterials, Apr. 2011, pp. 3233-3243.
Cross et al., Dense type I collagen matrices that support cellular remodeling and microfabrication for studies of tumor angiogenesis and vasculogenesis in vitro, Biomaterials, 2010, pp. 8596-8507, Elsevier, Ltd.
Deie et al., High intrinsic healing potential of human anterior cruciate ligament, Acta Orthopaedica Scandinavica, 1995, pp. 28-32, vol. 66(1).
Desrosiers et al., Proliferative and Matrix Synthesis Response of Canine Anterior Cruciate Ligament Fibroblasts Submitted to Combined Growth Factors, Journal of Orthopaedic Research, The Journal of Bone and Joint Surgery, Inc., 1996, pp. 200-208, vol. 14, No. 2.
Dye, Scott F. MD, The Future of Anterior Cruciate Ligament Restoration, Clinical Orthopaedics and Related Research, Apr. 1996, pp. 130-139, vol. 325.
Extended European Search Report, European Patent Application No. 13743583.0, Sep. 17, 2015, 7 pp.
Extended European Search Report, European Patent Application No. 06720499.0, Completed Jul. 7, 2009, 7 pp.
Australian Examination Report, Australian Patent Application 2017254864, Aug. 31, 2018, 7 pp.
Partial European Search Report, European Patent Application 14745975.4, Aug. 26, 2016, 7 pp.
International Preliminary Report on Patentability, PCT/US2013/024467, Aug. 5, 2014, 7 pp.
Faryniarz et al., Myofibroblasts in the Healing Lapine Medical Collateral Ligament: Possible Mechanisms of Contraction, Journal of Orthopaedic Research, The Journal of Bone and Joint Surgery, Inc., 1996, pp. 228-238, vol. 14, No. 2.
Ferber, Dan, Lab-Grown Organs Begin to Take Shape, Science, Apr. 1999, 6 pp., The American Association for the Advancement of Science, vol. 284, No. 5413.
Ferber, Dan, Tissue Engineering: From the Lab to the Clinic, Science, Apr. 1999, 2 pp., The American Association for the Advancement of Science, vol. 284, No. 5413.
Ford et al., Autologous Collagen Vocal Fold Injection: A Preliminary Clinical Study, Sep. 1995, 944-948, aryngoscope 105.
Frank et al., Natural History of Healing in the Repaired Medial Collateral Ligament, Journal of Orthopaedic Research, Orthopaedic Research Society, 1983, pp. 179-188, vol. 1, No. 2.
Geiger, et al., An In Vitro Assay of Anterior Cruciate Ligament (ACL) and Medial Collateral Ligament (MCL) Cell Migration, Connective Tissue Research, 1994, pp. 215-224, vol. 30. Gordon and Breach Science Publishers, S.A.
Gerich et al., Gene transfer to the patellar tendon, Knee Surg., Sports Traumatol, Arthroscopy, 1998, pp. 118-123, Springer-Verlag.
Gwinn et al., Relative Gender Incidence of Anterior Cruciate Ligament Injury at a Military Service Academy, 66th Annual Meeting of the American Academy of Orthopaedic Surgeons, Anaheim, CA, 1999, 1 pp., Paper No. 143.
Hefti et al., Healing of the Transected Anterior Cruciate Ligament in the Rabbit, The Journal of Bone and Joint Surgery, Mar. 1991, pp. 373-383, vol. 73-A, No. 3.
Itoh et al., Characterization of CO3AP-collagen sponges using X-ray high-resolution microtomography, Biomaterials, 2004, pp. 2577-2583, vol. 25.
Jackson et al., Biologic remodeling after anterior cruciate ligament reconstruction using a collagen matrix derived from demineralized bone: an experimental study in the goat model, The American Journal of Sports Medicine, Jul.-Aug. 1996, 15 pp., vol. 24, No. 4.
Juncosa-Melvin et al., The Effect of Autologous Mesenchymal Stem Cells on the Biomechanics an Histology of Gel-Collagen Sponge Constructs Used for Rabbit Patellar Tendon Repair, Tissue Engineering, 2006, pp. 370-380, vol. 12.
Kanungo et al., Density-property relationships in mineralized collagen-glycosaminoglycan scaffolds, Aug. 26, 2008, pp. 1006-1018, Acta Biomaterials 5, Elsevier.
Kato et al., Formation of continuous collagen fibres: evaluation of biocompatibility ad mechanical properties, Biomaterials, Apr. 1990, pp. 169-175, vol. 11, Butterworth & Co., Ltd (Publishers).
Kawamoto et al., Selective migration of alpha-smooth muscle actin-positive myofibroblasts toward fibronectin in the Boyden's blindwell chamber, Clinical Science, 1997, pp. 355-362, vol. 93.
Kliment et al., A novel method for accurate collagen and biochemical assessment of pulmonary tissue utilizing one animal, Int. J. Clin. Exp. Pathol., 2011, pp. 349-355.
Louie, Libby K., Effect of a Porous Collagen-Glycosaminoglycan copolymer on Early Tendon Healing in a Novel Animal Model, Jan. 10, 1997, 1 pp., Ph.D. Thesis, Massachusetts Institute of Technology.
Louie et al., Development of a Collagen-GAG Copolymer Implant for the Study of Tendon Regeneration, Materials Research Society Symposium Proceedings, 1994, pp. 19-24, vol. 331.
Louie et al., Healing of Tendon Defects Implanted with a Porous Collagen=GAG Matrix: Histological Evaluation, Tissue Engineering, 1997, pp. 187-195, vol. 3, No. 2.
Marshall et al., The Anterior Ligament Cruciate Ligament: A Technique of Repair and Reconstruction, Clinical Orthopaedics and Related Research, Sep. 1979, pp. 97-106, No. 143.
First Office Action and Search Report, Chinese Patent Application No. 201780036894.1, Feb. 9, 2021, 22 pp.
Brazil Office Action and Informal Translation, Brazilian Patent Application BR112018075986-4, May 11, 2021, 5 pp.

\* cited by examiner

INDIRECT METHOD OF ARTICULAR TISSUE REPAIR

RELATED APPLICATIONS

This application is a national stage filing under 35 U.S.C. § 371 of international application number PCT/US2017/040865, filed Jul. 6, 2017, which was published under PCT Article 21(2) in English and claims the benefit under 35 U.S.C. § 119(e) of U.S. provisional application No. 62/358,661, filed Jul. 6, 2016, each of which is incorporated by reference herein in its entirety.

BACKGROUND OF THE INVENTION

Intra-articular tissues, such as the anterior cruciate ligament (ACL), do not heal after rupture. In addition, the meniscus and the articular cartilage in human joints also often fail to heal after an injury. Tissues found outside of joints heal by forming a fibrin clot, which connects the ruptured tissue ends and is subsequently remodeled to form scar, which heals the tissue. Inside a synovial joint, a fibrin clot either fails to form or is quickly lysed after injury to the knee, thus preventing joint arthrosis and stiffness after minor injury. Joints contain synovial fluid which, as part of normal joint activity, naturally prevent clot formation in joints. This fibrinolytic process results in premature loss of the fibrin clot scaffold and disruption of the healing process for tissues within the joint or within intra-articular tissues.

The current treatment method for human anterior cruciate ligament repair after rupture involves removing the ruptured fan-shaped ligament and replacing it with a point-to-point tendon graft (ACL reconstruction). While this procedure can initially restore gross stability in most patients, longer follow-up demonstrates many post-operative patients have abnormal structural laxity, suggesting the reconstruction may not withstand the physiologic forces applied over time (Dye, 325 Clin. Orthop. 130-139 (1996)). The loss of anterior cruciate ligament function has been found to result in early and progressive radiographic changes consistent with joint deterioration (Hefti et al., 73A(3) J. Bone Joint Surg. 373-383 (1991)), and over 70% of patients undergoing ACL reconstruction develop osteoarthritis at only 14 years after injury (von Porat et al., Ann Rheum Dis. 63(3):269-73 (2004)). As anterior cruciate ligament rupture is most commonly an injury of young athletes in their teens and twenties, early osteoarthritis in this group has difficult consequences.

In addition, anterior cruciate ligament reconstruction currently requires use of a tendon graft, harvested either from elsewhere in the patient's leg, or from a donor. Placement of this graft requires the removal of a large amount of the torn anterior cruciate ligament, thus removing the important proprioceptive nerve fibers which are important for ligament function, namely the dynamic stabilization of the knee. Placement of the graft is also recommended to be within the insertion site of the original anterior cruciate ligament, thus these zones of specialized tissue are also removed to create a tunnel for the graft.

Synthetic replacements for ligaments have also been developed. These include grafts made of carbon fiber, Gore-Tex and other synthetic materials. For grafts made of either natural materials or synthetic materials, the fibers of the graft are oriented such that they are parallel to the lines of tension in the ligament, that is in the direction of the long axis of the ligament. These formations allow the construct to support the tensile load during healing.

SUMMARY OF THE INVENTION

It has been discovered herein, in some aspects of the invention, that multiple small scaffolds, none of which connects from ligament end to ligament end, when surgically placed can be used effectively to repair injured ligament and tendon tissue. These findings were quite surprising. There is an expectation in the art that multiple scaffold pieces would not provide sufficient strength to be able to support the tensile load placed on the healing ligament or tendon. The finding that two or more discreet scaffolds placed in the area of the injury could actually augment ligament or tendon repair was unexpected.

In some embodiments the scaffolds are designed to be positioned along and optionally slide along a containment device such as a suture. The containment device may be used to move the scaffolds into the desired location in the wound site of the ligament or tendon and to retain them there as a group. For instance, when the containment device is a suture, the suture may be fixed to bone tissue on either side of the injured tissue. For instance in the repair of an anterior cruciate ligament the suture may be attached to the femur and tibia, typically at sites outside the attachment sites of the anterior cruciate ligament. For ligaments, typically one end of the suture would be attached to one bone (for example, the femur) and the other end would be attached to a different bone (for example, the tibia).

In some aspects the invention is a device for ligament or tendon repair comprising a containment device with multiple distinct biodegradable scaffolds positioned on the containment device. In some embodiments the containment device is a suture and the scaffolds are positioned along the length of the suture and are able to slide along the suture. In other embodiments the scaffolds are beads. The device for ligament or tendon repair may include, in some embodiments any of: 2-30, 2-50, 2-100, 5-10, 5-20, 5-50, 5-100, 5-200, 10-20, 10-30, 10-40, 10-50, 10-60, 10-70, 10-80, 10-90, 10-100, 15-20, 15-30, 15-50, 15-100, 20-30, 0-40, 20-50, 20-100, or 20-200 scaffolds.

In other embodiments, the body provides the containment for the multiple scaffolds. An example would be the intercondylar notch of the distal femur, into which the multiple scaffolds can be placed to fill or partially fill the notch. In some embodiments, these scaffolds can be placed through an arthrotomy. In some embodiments, these scaffolds can be placed arthroscopically.

In other aspects, the invention is a kit. The kit includes any of the above described devices and instructions for surgical repair of a ligament or tendon using the device. The kit may also include arthroscopic instruments to facilitate placement of the scaffolds through small incisions.

In some aspects a device for ligament or tendon repair is provided according to the invention. The device is a set of distinct biodegradable scaffolds, wherein the set of scaffolds comprises 2-30 scaffolds, and wherein the scaffolds are 1-50 mm in length. In some embodiments the scaffolds are compressible expandable scaffolds. In other embodiments the scaffolds are collagen sponges. In yet other embodiments the collagen sponges comprise type I soluble collagen and wherein the collagen sponges are prepared from a solution of solubilized collagen in a concentration of greater than 5 and less than or equal to 50 mg/ml. In yet other embodiments the collagen sponges comprise type I soluble collagen and wherein the collagen sponges are prepared from a solution of solubilized collagen in a concentration of greater than 50 and less than or equal to 500 mg/ml. In some embodiments, the solution contains calcium.

Each of the scaffolds in the set are the same in some embodiments. In other embodiments, at least one of the scaffolds in the set is different from the other scaffolds in the set. In some embodiments the at least one different scaffold has a different size than the other scaffolds. For instance, the at least one different scaffold may be larger than the other scaffolds or the at least one different scaffold may be smaller than the other scaffolds. In some embodiments the at least one different scaffold has a different shape than the other scaffolds. In yet other embodiments the at least one different scaffold is shaped as a sphere (e.g., beads) or a cylinder.

In some embodiments the at least one different scaffold is comprised of a different biodegradable polymer than the other scaffolds. For instance, the scaffolds may be comprised of collagen or the scaffolds may be comprised of a non-collagen polymer.

In some embodiments the set of scaffolds have a total surface area that is greater than a single scaffold used to repair a ligament or tendon injury. For example, a comparison of one cylinder having 3000 units of volume, to four smaller cylinders to deliver the same volume demonstrates that the four cylinders have almost double the surface area of the original scaffold. The first cylinder has the following dimensions: 20 mm diameter by 30 mm in length–volume is 3000*pi mm3 (pi*100*30). The four small cylinders have the following dimensions: Each is 10 mm in diameter and 30 mm in length–volume of each is 750*pi mm3. The surface area of the first cylinder is 800*pi and the surface area of each of the four small cylinders is 350*pi, with the total surface area being 1400*pi.

In yet other aspects the invention is a kit of any of the devices described herein and further comprising one or more containers to house the set of distinct biodegradable scaffolds, and instructions for surgical repair of a ligament or tendon using the device. In some embodiments the kit further includes a containment device housed in one or more of the containers. In some embodiments the containment device is a suture and the scaffolds are threaded onto the suture.

A method for repairing a ligament or tendon by placing a set of distinct biodegradable scaffolds positioned on a containment device into a site of an injured ligament or tendon to repair the ligament or tendon is provided in other aspects of the invention. In some embodiments the containment device is attached directly or indirectly to a bone on either side of the injured ligament or tendon. In yet other embodiments the containment device is a suture having at least two ends. One end of the suture may be attached to a first fixation device. In some embodiments a second end of the suture is attached to a second fixation device. In yet other embodiments the first fixation device is fixed to a femur and the second first fixation device is fixed to a tibia. In yet other embodiments, one end of the suture is attached to one bone (i.e. the femur) and the second end of the same suture is attached to a second bone (i.e. the tibia). The attachments of the suture to the two different bones may be direct or indirect.

A method for rotator cuff tendon repair of an injury by attaching a first fixation device to a humerus at a location other than an insertion site of the rotator cuff tendon, attaching a second fixation device to the tendon at a location remote from the injury site, and connecting a flexible construct to the two fixation devices is provided in other aspects of the invention. In some embodiments, the flexible construct is a suture. In some embodiments, the suture is absorbable and in some embodiments, the suture is nonabsorbable. In some embodiments, the suture configuration itself is used as the fixation method in the tendon. In some embodiments, this is a locking suture passage.

In some embodiments a scaffold is placed on the flexible construct so that the scaffold rests between the torn ends of the rotator cuff tendon without mechanically attaching the scaffold to the rotator cuff tendon. In some embodiments more than one flexible construct is placed between the first and second fixation devices. In other embodiments more than one scaffold is loaded onto the flexible constructs so that the scaffolds rest between the torn ends of the rotator cuff tendon without mechanically attaching the scaffolds to the rotator cuff tendon or to each other.

In other aspects the invention is a method for anterior cruciate ligament repair of an injury comprising attaching a first fixation device to a femur at a location other than an insertion site of the ligament, attaching a second fixation device to a tibia at a location remote from the insertion site of the ligament, and connecting a flexible construct to the two fixation devices.

A method for anterior cruciate ligament repair of an injury by placing a set of distinct biodegradable scaffolds into an intra-articular notch to repair an injured ligament is provided in other aspects of the invention. The scaffolds are not connected to one another, to the injured ligament or to tissue surrounding the injured ligament.

The invention relates in some aspects to methods and products that facilitate ligament healing, including healing of the anterior cruciate ligament, without further damaging the injured anterior cruciate ligament and without use of a tendon graft. Thus, in some aspects the invention is a device for repairing a ruptured anterior cruciate ligament comprising two suture ends fixed to the femur outside the anterior cruciate ligament attachment site. Two or more scaffolds are sequentially delivered, one along each suture end, into the intercondylar notch of the knee. The suture ends are then fixed to the tibia.

In some embodiments the scaffold is made of protein, such as, for example, a synthetic, bioabsorbable, or a naturally occurring protein. In other embodiments the scaffold is a lyophilized material. The scaffold may be expandable. In other embodiments the scaffold may be a sponge, a gel, a solid, or a semi-solid. The scaffold may be pretreated with a repair material. Repair materials include but are not limited to gels, liquids, and hydrogels.

In some embodiments, more than two suture ends are used. In some embodiments, more than two scaffolds are used. The multiple scaffolds could be of the same size or of varying sizes. In some embodiments, sutures are attached to the femoral bone at two locations. In some embodiments, sutures are attached to the tibial bone at two locations.

A method of repairing a ruptured ligament that involves anchoring sutures at two different sites in the intercondylar notch of the femur, sequentially passing two or more scaffolds into the intercondylar notch and then securing the sutures at two different sites to the tibia.

A method of repairing a ruptured ligament that involves anchoring sutures at two different sites in the intercondylar notch of the femur, sequentially passing two or more scaffolds into the intercondylar notch and then securing the sutures at one site of the tibia. In some embodiments, the sutures are secured to the tibia with the knee in full extension. In some embodiments, the tension is placed on the sutures prior to fixing them at the second bone site. In some embodiments, the sutures are fixed to the femur, the scaffolds passed along the sutures and the sutures tensioned and fixed to the tibia under tension. In the preferred embodiment, the sutures are fixed to the femur, scaffolds placed into the notch, sutures passed through a tibial tunnel, the sutures are tensioned to reduce the knee and then the sutures are fixed under tension to maintain the reduction of the tibia under the femur.

A method of repairing a ruptured ligament that involves fixing the sutures at one site in the intercondylar notch of the femur, sequentially passing two or more scaffolds into the intercondylar notch and then securing the sutures at two sites to the tibia.

The scaffold in some embodiments is made from a protein. The protein may be synthetic, bioabsorbable, or a naturally occurring protein. In some embodiments the scaffold can absorb plasma, blood, or other body fluids.

In other embodiments the scaffold is tubular, semi-tubular, cylindrical, spherical or square. The scaffold is a sponge or a gel in some embodiments. In other embodiments the scaffold is a semi-solid or, alternatively, a solid.

In yet other embodiments the scaffolds are expandable. They may optionally fill the repair site. In some embodiments the scaffolds are bigger than the repair site and in other embodiments the scaffolds partially fill the repair site. The scaffolds may form around the ligament at the repair site. The scaffolds may be pretreated with a repair material, such as a gel or a liquid. In some embodiments the repair material is a hydrogel. In other embodiments the repair material is collagen.

In yet other embodiments the scaffold is compressible. It may optionally fill the repair site. In some embodiments the scaffold is bigger than the repair site and in other embodiments the scaffold partially fills the repair site. The scaffold may form around the ligament at the repair site. The scaffold may be pretreated with a repair material, such as a gel or a liquid. In some embodiments the repair material is a hydrogel. In other embodiments the repair material is collagen. In other embodiments, the repair material comprises a platelet. In other embodiments, the repair material comprises whole blood or any of its cellular components. In other embodiments, the repair material is autologous blood. In other embodiments, the repair material is composed of white blood cells, red blood cells, platelets or plasma. In other embodiments, the repair material is composed of monocytes, eosinophils, basophils or neutrophils. In other embodiments, the repair material is composed of autologous blood which has been treated after removal from the patient to increase the presence of a specific type of white blood cell within the repair material. In one embodiment, the blood has been treated to increase the presence of monocytes in the repair material. In other embodiments, the patient has been treated prior to surgery to increase the presence of white blood cells and/or platelets in the circulating blood that is drawn to use for the repair material.

A method of repairing a ruptured ligament that involves drilling a hole adjacent to the insertion site of a ruptured ligament and attaching suture to the bone through the hole is provided in some aspects of the invention. The method involves attaching one or more sutures to the bone using an anchor, staple, screw, button or similar fixation device.

A method where two or more sutures are fixed to the femur, and one or more scaffolds are slid along the suture into the intercondylar notch, and the sutures are fixed to the tibia. In one embodiment, after placement of the sutures and scaffold and anchoring of the sutures to femur and tibia, an additional suture is placed into the tibial stump of the torn ACL and fixed to the femur in addition to the femur-tibia sutures. In another embodiment, after placement of the sutures and scaffold and anchoring of the sutures to femur and tibia, an additional suture is placed into the femoral stump of the ACL and secured to the tibia. In another embodiment, all fixation devices are located in the femoral and tibial epiphyses. In another embodiment, the femoral fixation device is located in the femoral epiphysis and the tibial fixation device is located in the tibial metaphysis.

A method where tunnels are drilled in the tibia and femur and a suture placed in the stump of the torn ACL and passed through the femoral tunnel for a tibial stump suture or through the tibial tunnel for a femoral stump suture. This may be done before, during or after placement of a suture anchored to the femoral and tibial bones. After passage of the suture through the bone tunnel, it is fixed to the bone using an anchor, staple, screw, button or other similar fixation device. In another embodiment, the suture placed in the stump of the ACL is anchored to the femoral bone for a tibial stump or the tibial bone for a femoral stump using a fixation device such as an anchor, staple, screw or button. This may be done before, during or after placement of a suture anchored to the femoral and tibial bones.

In some embodiments, the fixation device is bioabsorbable, metal, plastic, etc. In other embodiments, the fixation device is a screw. In certain embodiments, the fixation device has a suture attached to it directly or through a hole drilled in the fixation device. In some embodiments, the suture is a bioabsorbable, synthetic etc. In other embodiments, the suture is polyglactin 910.

In some embodiments, the scaffold is synthetic, bioabsorbable, or a naturally occurring protein. In certain embodiments, the scaffold can absorb plasma, blood, or other body fluids. In other embodiments, the scaffold is tubular, semi-tubular, cylindrical, or square. In certain embodiments, the scaffold is pretreated with a repair material. In some embodiments, the repair material is a gel or a liquid. In other embodiments, the repair material is hydrogel. In some embodiments, the repair material is collagen.

In some embodiments, the scaffold is a sponge. In certain embodiments, the scaffold is a gel. In other embodiments, the scaffold is a semi-solid. In some embodiments, the scaffold is a solid.

In some embodiments, the scaffold is freely moveable on the suture material. The scaffolds may be connected to each other or separate. They may be separated or moved together during entry into the joint or once in the wound site.

In some embodiments, the scaffolds are in the form of a cylinder, the dimension of which may range from 1 mm diameter to 25 mm diameter and the length from 0.1 mm to 100 mm. The preferred embodiment is for the scaffold to range from 4 to 8 mm in diameter and from 10 to 20 mm in length. In other embodiments, the scaffolds are in the form of a sphere. The radius of the sphere can range from 0.1 mm to 50 mm, with the preferred embodiment having a radius from 2 to 4 mm. Other shapes with a volume ranging from 1 ml to 100 ml are also envisioned.

In some embodiments, the scaffolds are supplied as a device which contains a suture with the scaffolds already placed along the suture. In other embodiments, the scaffolds are placed along more than one suture. In the preferred embodiment, the suture is looped through a fixation device and the beads are placed on the two free ends of the suture. In the preferred embodiment, the scaffolds are able to freely slide on the suture material.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

BRIEF DESCRIPTION OF THE DRAWINGS

FIG. 2A shows a Button en face. FIG. 2B shows a side view of the button.

FIG. 3A shows the button suture passed thru button and femur drill hole. FIG. 3B shows the first scaffold passed along suture into notch. FIG. 3C shows the second scaffold passed along second suture. FIG. 3D shows sutures passed thru tibia and secured to tibia over second button.

FIG. 4A shows an anchor to which the suture is attached. The anchor is placed into the bone of the femur. FIG. 4B shows first scaffold passed along suture. FIG. 4C shows second scaffold passed along second suture. FIG. 4D shows sutures secured to tibia with button or other fixation device.

In FIG. 8A, the torn ACL is visualized. FIGS. 8B, 8C, and 8D demonstrate the appearance of the healing ACL at 3 months, 6 months and 12 months respectively.

FIG. 11A depicts scaffolds in the form of beads on 2 areas of a suture threaded between the tibia and femur. FIG. 11B depicts scaffolds in the form of beads on multiple areas of a suture threaded between one area of a bone and through the injured ligament into a second area of the bone. FIG. 11C depicts scaffolds in the form of beads on multiple areas of a suture threaded between one area of the bone and through the injured ligament into a second area of the bone, where the beads are pulled tightly into the gap between the bone and injured ligament.

DETAILED DESCRIPTION OF THE INVENTION

Figure 1:
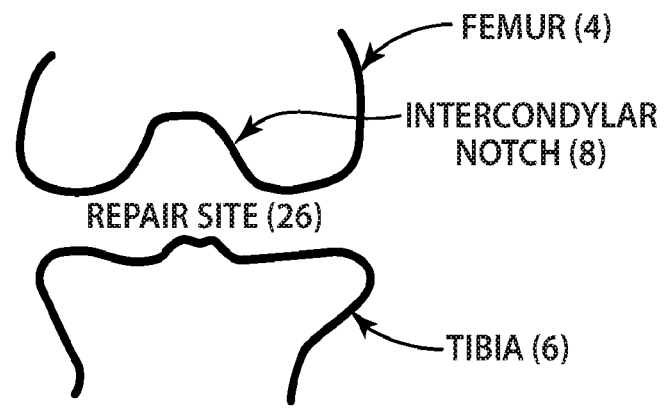
FIG. 1: Schematic illustrating a basic anatomy of the knee showing the distal femur, proximal tibia and location of the intercondylar notch.

Aspects of the invention relate to devices and methods for repairing an injured articular tissue. The device is, in some aspects, a set of scaffolds for repair of articular tissue. Prior to the invention it was believed that a single scaffold or other repair material was important for the promotion of healing in the repair of an injured tissue. It was expected that if repair material were torn or damaged that it would interfere with the healing process because it would lack the strength to promote the healing and because the exposed surface area of the material would be greater. It was discovered quite unexpectedly, that in contrast to the understanding in the prior art, the use of multiple distinct scaffolds enhances the healing of a damaged articular tissue.

Thus, the invention in some aspects relates to methods for repairing injured articular tissue using a set of distinct biodegradable scaffolds. A set of distinct scaffolds, as used herein refers to more than one scaffold. The scaffolds within the set may be identical to one another or they may have different properties. For instance, one or more of the scaffolds may have a different size or shape than the other scaffolds in the set. One or more of the scaffolds may be comprised of a different material or have a different concentration (e.g. concentration of collagen) or may have a different porosity or any other property. Each of the scaffolds in the set may be different from one another. Alternatively, any number of these scaffolds within the set may be different from one another.

The number of scaffolds within a set may vary. For instance, the set of scaffolds may be 2-100 scaffolds. The smaller the scaffolds, the larger the number may be. The set may include for instance, 2-90, 2-80, 2-70, 2-60, 2-50, 2-40, 2-30, 2-20, 2-10, 2-5, 3-90, 3-80, 3-70, 3-60, 3-50, 3-40, 3-30, 3-20, 3-10, 3-5, 4-90, 4-80, 4-70, 4-60, 4-50, 4-40, 4-30, 4-20, 4-10, 4-5, 5-90, 5-80, 5-70, 5-60, 5-50, 5-40, 5-30, 5-20, 5-10, 5-100, 10-90, 10-80, 10-70, 10-60, 10-50, 10-40, 10-30, 10-20, 10-100, 15-90, 15-80, 15-70, 15-60, 15-50, 15-40, 15-30, 15-20, 15-100, 20-90, 20-80, 270, 15-60, 15-50, 15-40, 15-30, 15-20, 15-100, 2-200, 3-200, 4-200, 5-200, 20-200, 100-200, 2-500, 3-500, 4-500, 5-500, 20-500, 100-500, 2-1,000, 3-1,000, 4-1,000, 5-1,100, 20-1,000, 100-1,000 or 500-1,000.

In some embodiments, one or more of the scaffolds may have a different property such as size or shape, comprised of a different material, comprised of a different concentration (e.g. concentration of collagen) or comprised of a different porosity than the other scaffolds in the set. In some embodiments 1%, 2%, 3%, 4%, 5%, 6%, 7%, 8%, 9%, 10%, 15%, 20%, 25%, 30%, 35%, 40%, 45%, 50%, 60%, 70%, 80%, 90% or 95% of the scaffolds have a different property than other scaffolds in the set. In other embodiments, the scaffolds in the set comprise at least 2 different properties. In other embodiments they comprise at least 3, 4, 5, 6, 7, 8, 9, or 10 different properties.

In some aspects the device of the invention for the repair of a ruptured ligament includes a scaffold which is configured for the repair of a ruptured ligament, a fixation device and at least one suture. The scaffold allows the subject's body to develop a network of capillaries, arteries, and veins. Well-vascularized connective tissues heal as a result of migration of fibroblasts into the scaffold. A device of the invention provides a connection between a ruptured ligament, or forms around a torn ligament, and promotes the repair of the ruptured or torn ligament while maintaining the integrity and structure of the ligament, without requiring the placement of damaging sutures into the ligament or damaging the ligament insertion site with a drill hole in the insertion site of the ACL. Rather, any sutures or other containment devices used in these embodiments of the invention are attached to surfaces other than the ligament or the site of attachment of the ligament to the bone.

A containment device, as used herein, refers to any material used to hold the scaffolds in an area for a period of time. For instance, sutures may be used to thread and hold a scaffold in place at the site of injury. Alternatively a biodegradable material such as a mesh or bag may be used to hold the scaffolds in place at the site of injury. In some embodiments the containment device is a tube or syringe that the scaffolds or powder is in. For instance the tube may be used to deliver the scaffolds with a plunger placed at the back of the tube.

The device of these embodiments provides a suture and at least one three-dimensional scaffold construct for repairing a ruptured or torn anterior cruciate ligament. The scaffold provides a connection between the ruptured ends of the ligament and fibers, or forms around a torn ligament, after injury, and encourages the migration of appropriate healing cells to form scar and new tissue in the scaffold.

Methods and devices of the invention may be used to treat either intra-articular or extra-articular injuries in a subject. Intra-articular injuries include, but are not limited to, meniscal tears, ligament tears, tendon tears and cartilage lesions. Extra-articular injuries include, but are not limited to, the ligament, tendon or muscle. Thus, the methods of the invention may be used to treat injuries to the anterior cruciate ligament, the meniscus, labrum, rotator cuff tendon, glenoid labrum and acetabular labrum, cartilage, and other tissues exposed to synovial fluid after injury.

An injury may be a torn or ruptured ligament. A torn ligament is one where the ligament remains connected but has been damaged causing a tear in the ligament. The tear may be of any length or shape. A ruptured ligament is one where the ligament has been completely severed providing two separate ends of the ligament. A ruptured ligament may provide two ligament ends of similar or different lengths. The rupture may be such that a ligament stump is formed at one end.

An example of a repair site (26) of a ruptured anterior cruciate ligament can be seen in the schematic illustrating a basic anatomy of the knee showing the distal femur, and proximal tibia depicted in FIG. 1. The anterior cruciate ligament (ACL) is one of four strong ligaments that connects the bones of the knee joint. The function of the ACL is to provide stability to the knee and minimize stress across the knee joint. It restrains excessive forward movement of the lower leg bone, the tibia (6), in relation to the thigh bone, the femur (4), and limits the rotational movements of the knee. An anterior cruciate ligament is ruptured such that it no longer forms a connection between the femur bone (4) and the tibia bone (6) in the intercondylar region (8). The resulting ends of the ruptured ACL may be of any length. The ends may be of a similar length, or one end may be longer in length than the other.

A scaffold of the device of the invention can be any shape that is useful for implantation into a subject. The scaffold, for instance, can be tubular, semi-tubular, cylindrical, including either a solid cylinder or a cylinder having hollow cavities, a tube, a flat sheet rolled into a tube so as to define a hollow cavity, liquid, an amorphous shape which conforms to that of the repair space, a "Chinese finger trap" design, a trough shape, or square or a sphere (bead). Other shapes suitable for the scaffold of the device as known to those of ordinary skill in the art are also contemplated in the invention.

Figures 2A, 2B:
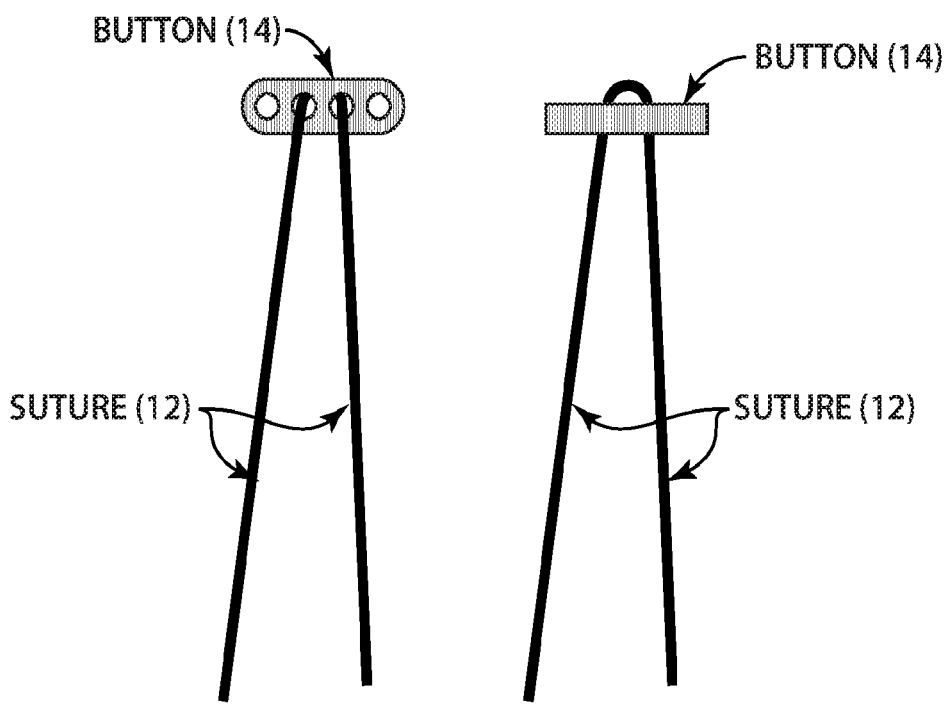
FIGS. 2A-2B: Schematic illustrating how one suture can be passed through two holes of a fixation button to provide two suture ends for indirect ligament repair. A suture is passed through one hole of a button and back through a second hole to anchor the suture, leaving two free suture ends which can exit the bone into the joint at a location distinct from the ligament insertion site.
Figure 3A:
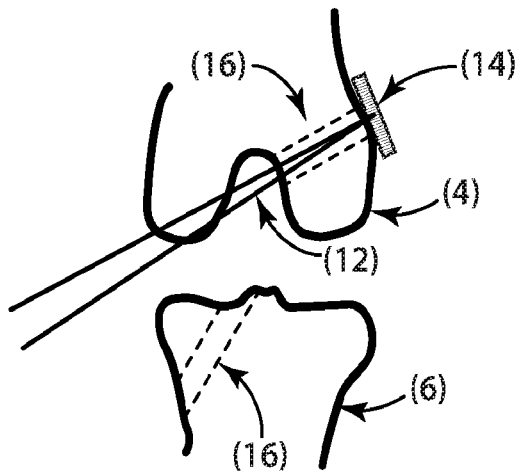
FIGS. 3A-3D: Schematic illustrating one method of beaded ligament repair with an indirect method of attaching the suture to the femur and tibia.
Figure 3B:
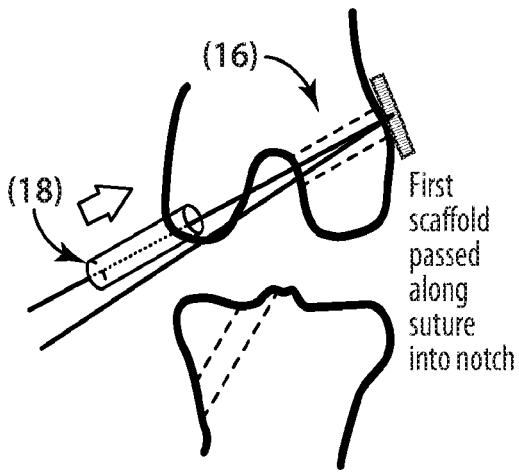
Figure 3C:
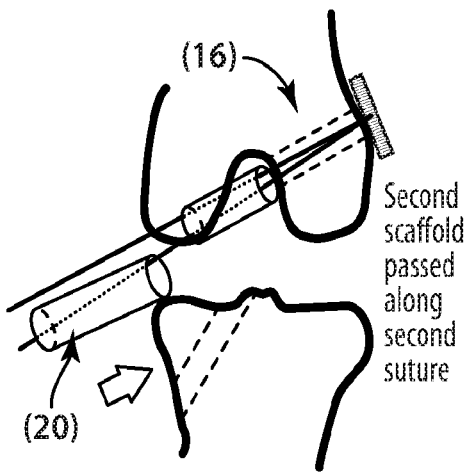
Figure 3D:
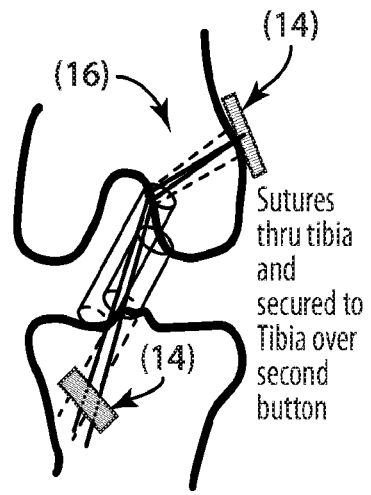
Figure 4A:
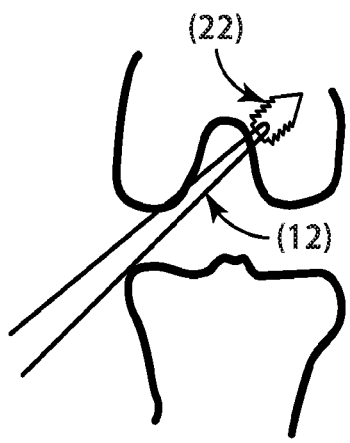
FIGS. 4A-4D: Schematic illustrating one other method of indirect ligament repair.
Figure 4B:
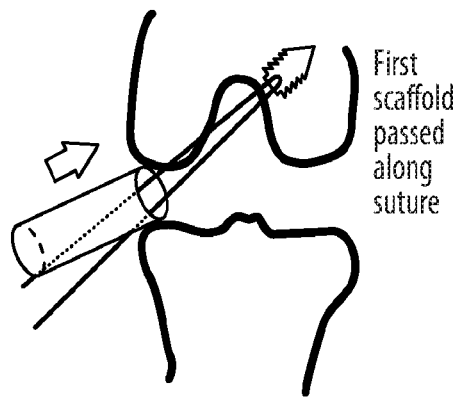
Figure 4C:
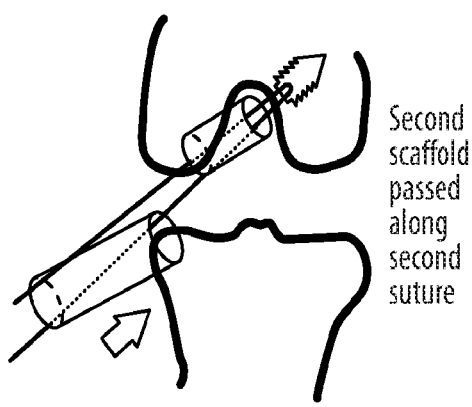
Figure 4D:
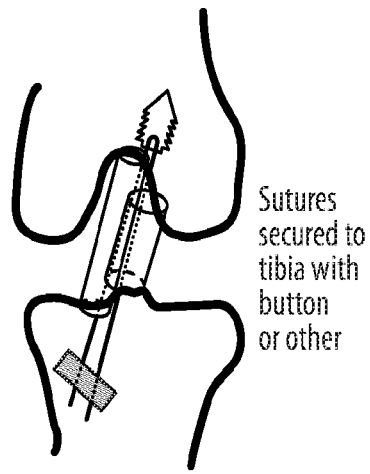

A schematic illustrating a basic anatomy of the knee is shown in FIG. 1. Examples of devices and systems useful according to the invention are depicted in FIGS. 2-6. Exemplary surgical methods are also shown pictorially in FIG. 7. A suture (12) may be passed through one hole of a button (14) and back through a second hole to anchor the suture, leaving two free suture ends which can exit the bone into the joint at a location distinct from the ligament insertion site (FIGS. 2A-2B). FIG. 2A shows a Button en face. FIG. 2B shows a side view of the button.

FIGS. 3-6 show examples of surgical methods performed with multiple scaffolds. For instance, FIGS. 3A-3D show one method of multiple scaffold ligament repair. First, drill holes (16) are created in the femur (4) and tibia (6), with care taken not to have these injure the anterior cruciate ligament insertion sites on each bone or the ligament itself. Then a suture (12) is placed over a button (14) as illustrated in FIG. 2 and the button passed up through the femoral tunnel and flipped to anchor the two suture ends on the femur. The first scaffold (18) is then passed along one of the suture ends and up into the intercondylar notch. The second scaffold (20) is then passed along the second suture up into the notch. The suture ends are then brought through a tibial tunnel and secured to the tibia by tying the ends over a button or using another fixation device.

Another method of indirect ligament repair is shown in FIGS. 4A-4D. First, an anchor (22) with two free suture ends is placed in the femur, with care taken not to have this injure the anterior cruciate ligament insertion sites on the femur or the ligament itself. The first scaffold is then passed along one of the suture ends and up into the intercondylar notch. The second scaffold is then passed along the second suture up into the notch. The suture ends are then brought through a tibial tunnel and secured to the tibia by tying the ends over a button or using another fixation device.

Figure 5:
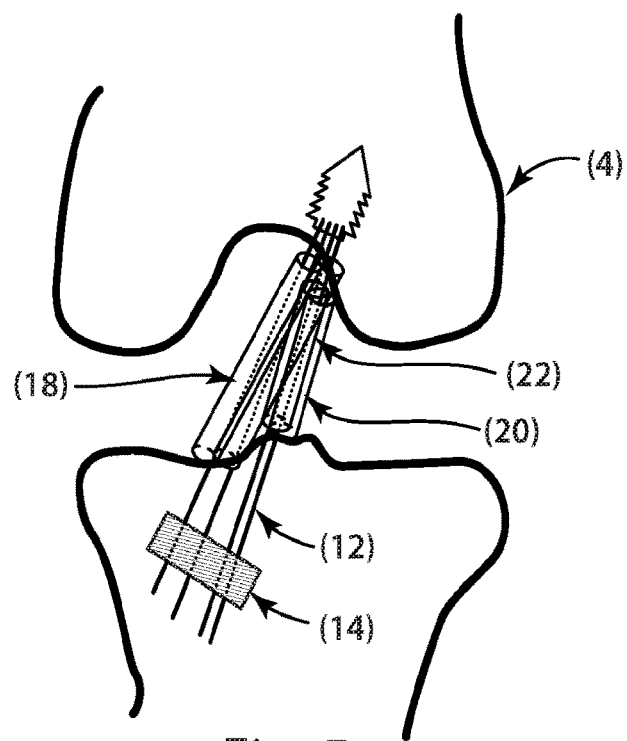
FIG. 5: Schematic illustrating another exemplary method of indirect tissue repair. First, an anchor with more than two free suture ends is placed in the femur, with care taken not to have this injure the anterior cruciate ligament insertion sites on the femur or the ligament itself. The first scaffold is then passed along one of the suture ends and up into the intercondylar notch. The second scaffold is then passed along the second suture up into the notch. Additional scaffolds are placed along additional sutures. The suture ends are then brought through a tibial tunnel and secured to the tibia by tying the ends over a button or using another fixation device.

FIG. 5 shows another exemplary method of indirect tissue repair. First, an anchor (22) with more than two free suture ends is placed in the femur, with care taken not to have this injure the anterior cruciate ligament insertion sites on the femur or the ligament itself. The first scaffold (18) is then passed along one of the suture ends and up into the intercondylar notch. The second scaffold (22) is then passed along the second suture up into the notch. Additional scaffolds are placed along additional sutures. The suture ends are then brought through a tibial tunnel and secured to the tibia by tying the ends over a button (14) or using another fixation device.

Figure 6:
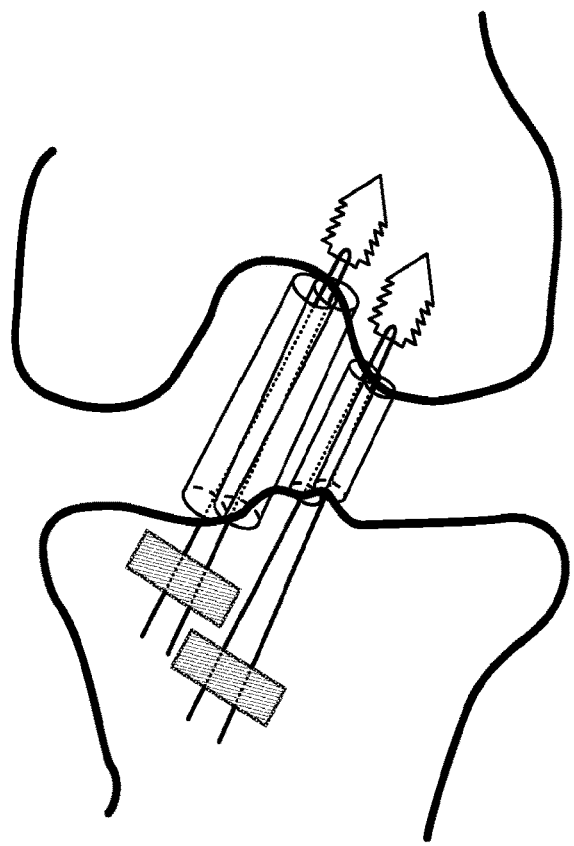
FIG. 6: Schematic illustrating one other method of indirect ligament repair. First, two anchors, each with two free suture ends are placed in the femur, with care taken not to have these injure the anterior cruciate ligament insertion sites on the femur or the ligament itself. The first scaffold is then passed along one of the suture ends and up into the intercondylar notch. The second scaffold is then passed along the second suture up into the notch. Additional scaffolds are placed along additional sutures. The suture ends are then brought through a tibial tunnel and secured to the tibia by tying the ends over a button or using another fixation device. Two or more tibial tunnels or fixation devices may also be used. Two or more femoral tunnels or fixation devices may also be used.

A method of indirect ligament repair is also shown in FIG. 6. First, two anchors (22), each with two free suture (12) ends are placed in the femur (4), with care taken not to have these injure the anterior cruciate ligament insertion sites on the femur or the ligament itself. The first scaffold is then passed along one of the suture ends and up into the intercondylar notch. The second scaffold is then passed along the second suture up into the notch. Additional scaffolds are placed along additional sutures. The suture ends are then brought through a tibial tunnel and secured to the tibia by tying the ends over a button or using another fixation device. Two or more tibial tunnels or fixation devices may also be used.

Figure 11A:
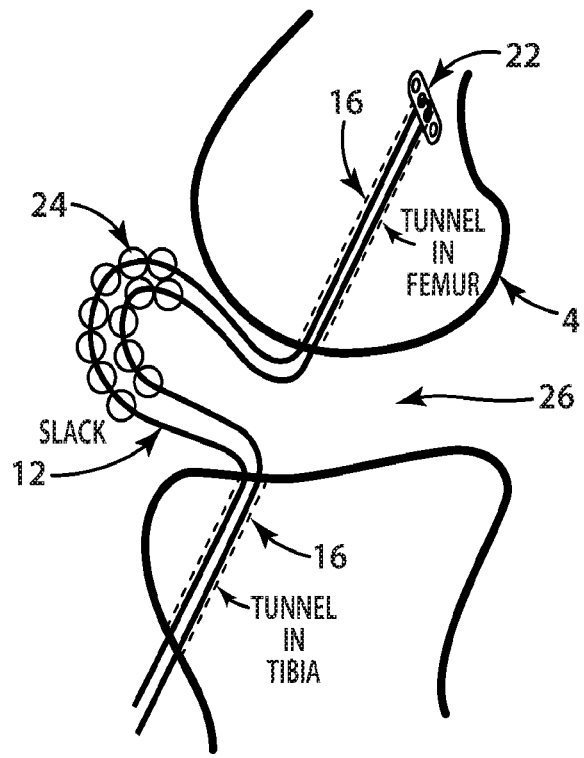
FIGS. 11A-11C: Schematic illustrating an exemplary method for repairing an ACL using multiple scaffolds.
Figure 11B:
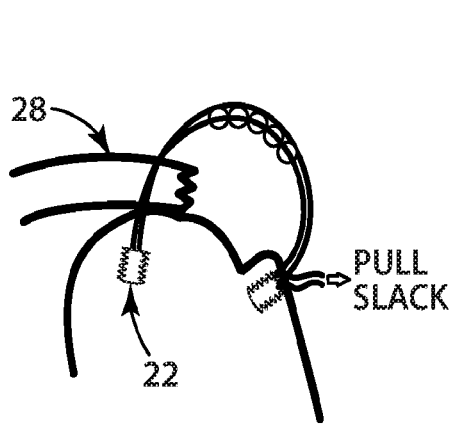
Figure 11C:
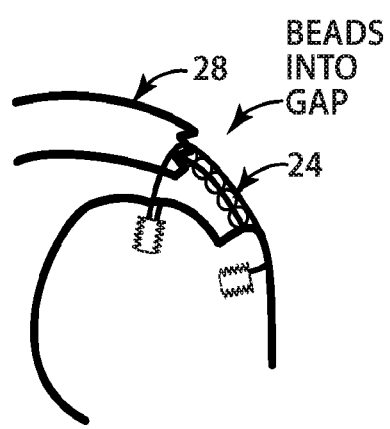

FIGS. 11A, 11B and 11C illustrate an exemplary method for repairing an ACL using multiple scaffolds (24). Scaffolds (24) in the form of beads on 2 areas of a suture threaded between the tibia and femur is shown in FIG. 11A. The suture (12) is slack while threaded through the tunnels (16) in femur and tibia. The suture may be pulled tight and secured by anchors (22) or other devices. FIG. 11B depicts an alternate embodiment in which scaffolds in the form of beads (24) on multiple areas of a suture (12) are threaded between one area of a bone (femur or tibia) and through an injured ligament (28) into a second area of the bone or the other bone. In FIG. 11C scaffolds in the form of beads on a suture are depicted as threaded tightly between one area of the bone and through the injured ligament such that the scaffolds fill the gap between the bone and the injured ligament (28).

Figure 12A:
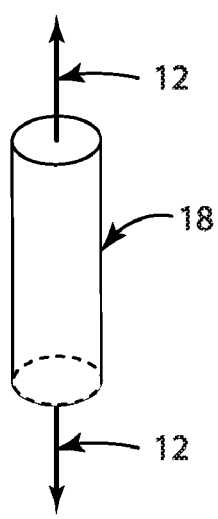
FIGS. 12A-12B: Schematic illustrating a standard ligament replacement scaffold (12A) and a set of distinct biodegradable scaffolds (12B).
Figure 12B:
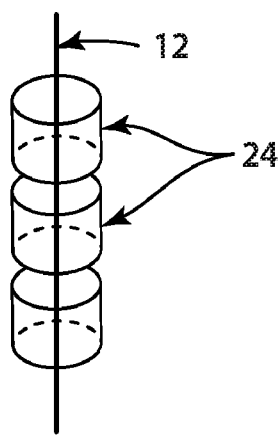

A representation of various scaffold configurations are depicted in FIGS. 12A and 12B. A standard ligament replacement scaffold (18) is shown threaded on a suture (12) in FIG. 12A. A set of distinct biodegradable scaffolds (24) are shown threaded on a suture (12) in FIG. 12B.

FIGS. 7A-7K is a set of photographs illustrating the use of an indirect repair technique using a single scaffold and incorporating a stitch in the tibial ACL stump. The methods can also be applied to multiple scaffolds, which may, for instance, be threaded along the suture.

Figure 7A:
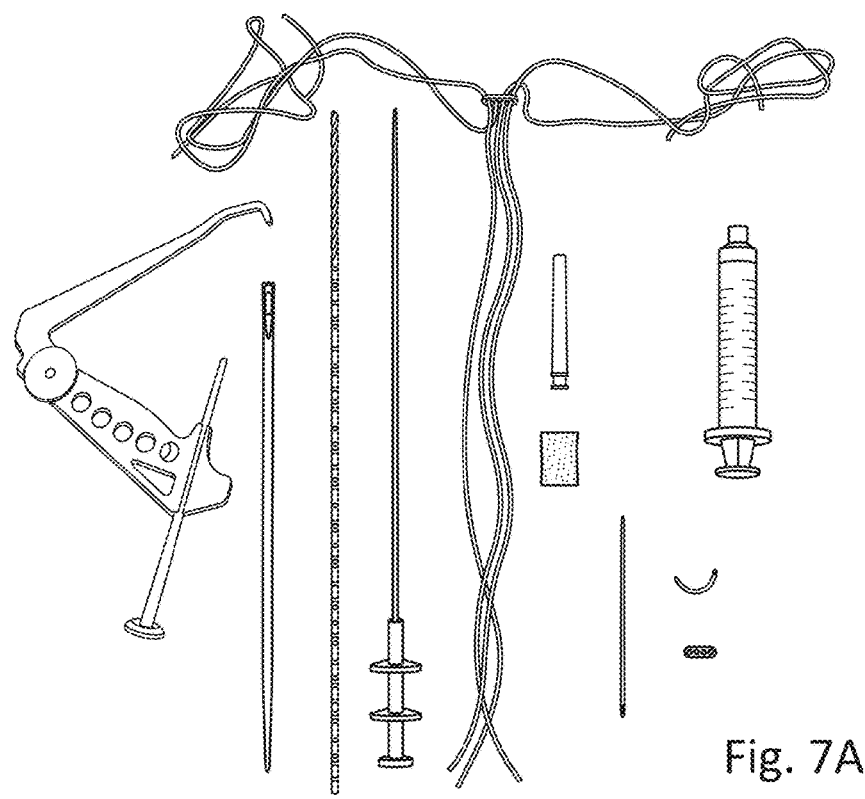
FIGS. 7A-7K: A set of photographs illustrating the use of an indirect repair technique using a single scaffold and incorporating a stitch in the tibial ACL stump.

FIG. 7A is a photograph showing equipment used in the surgical technique. This includes 2 Endobuttons, 2.4 mm Drill Pin, Endobutton Drill, Tibial Aimer, Suture Passer, Keith Needle, Mayo Needle, Foot Kit, and Scaffold.

Figure 7B:
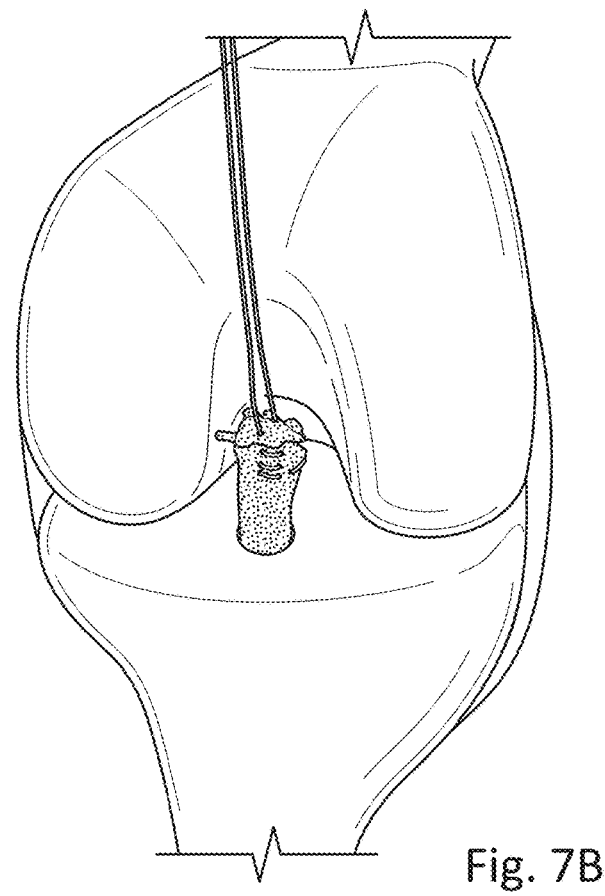
Figure 7C:
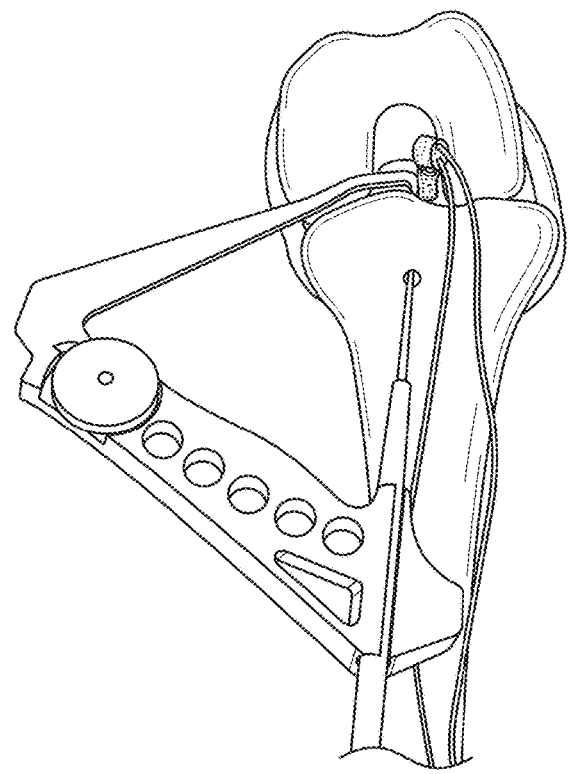
Figure 7D:
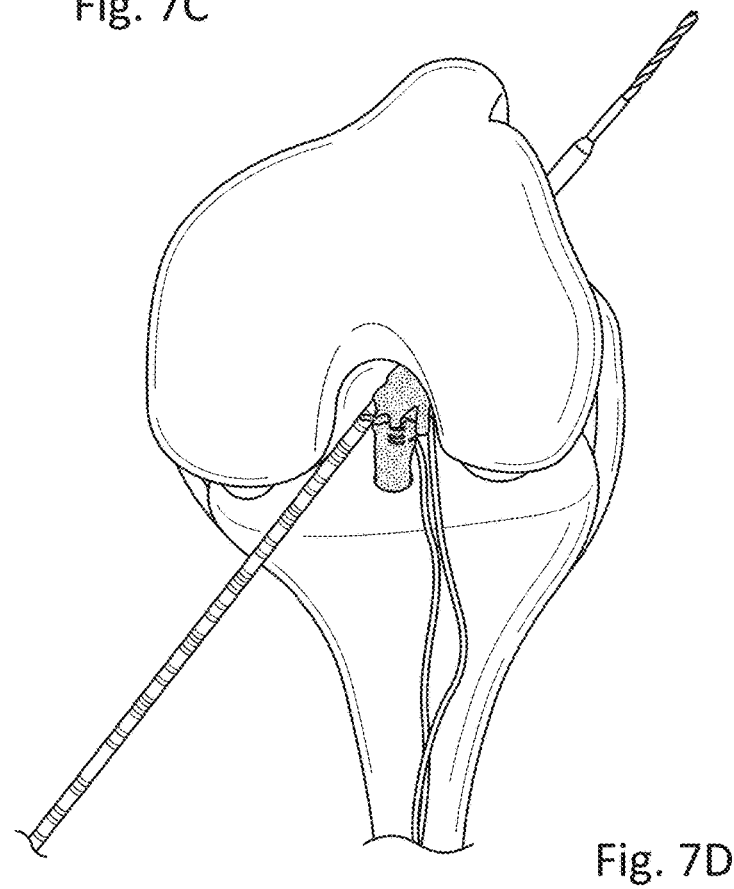
Figure 7E:
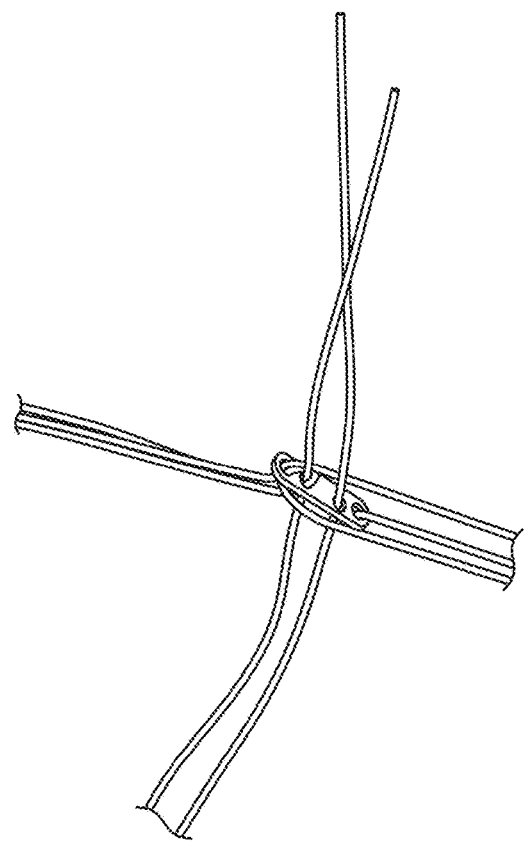
Figure 7F:
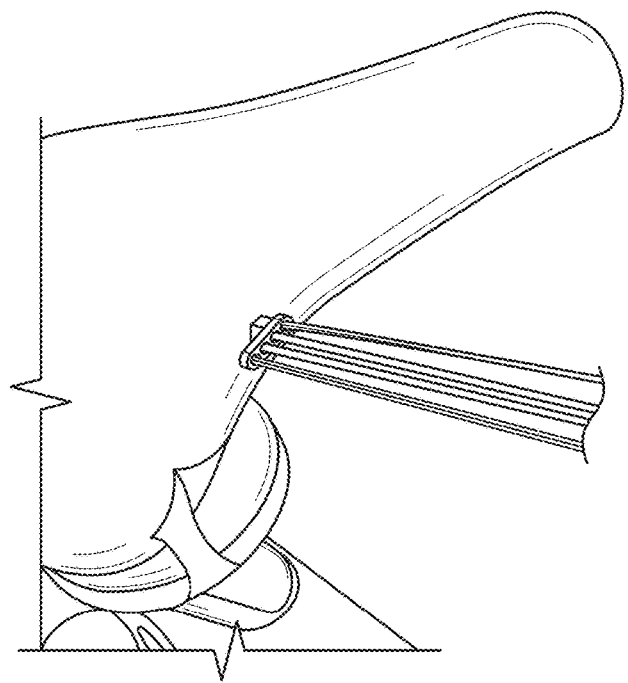
Figure 7G:
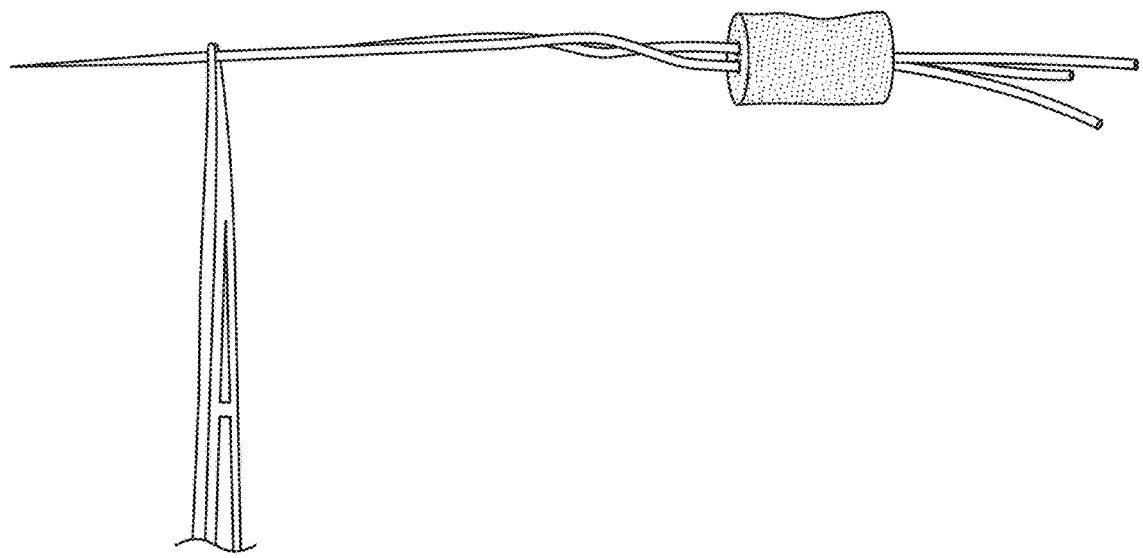
Figure 7H:
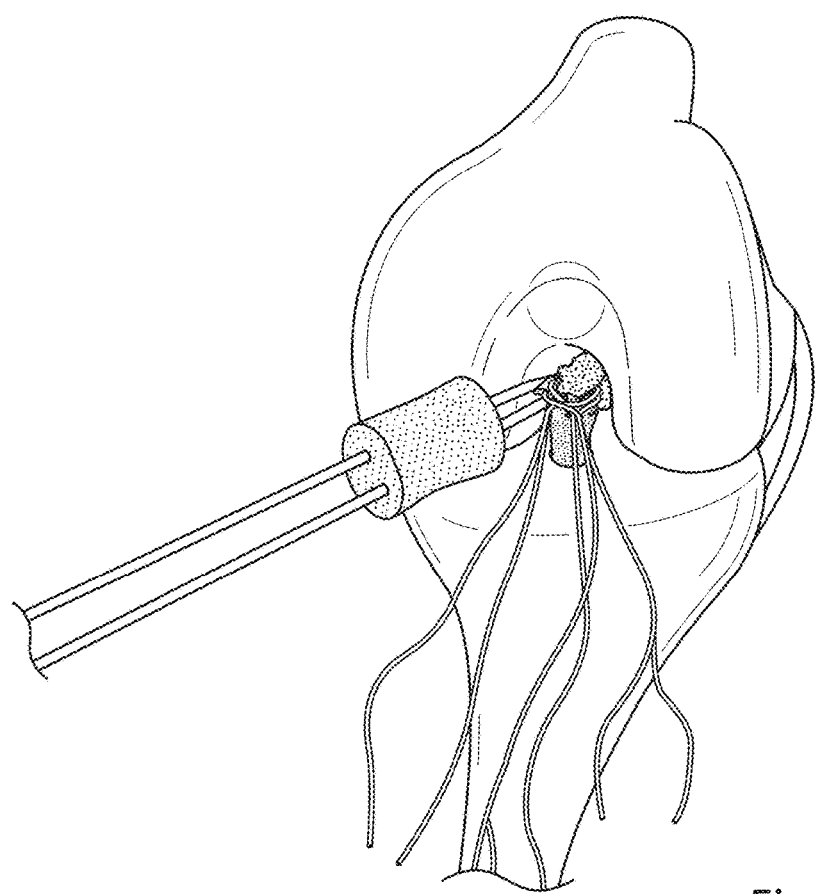
Figure 7I:
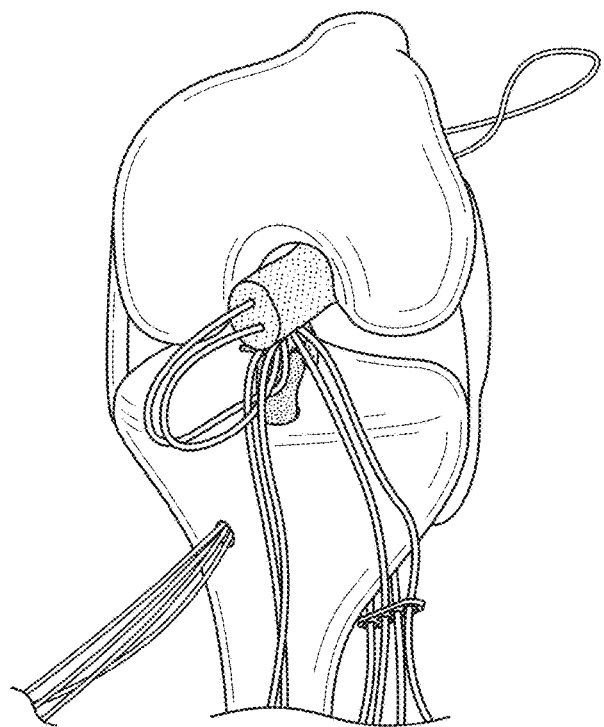
Figure 7J:
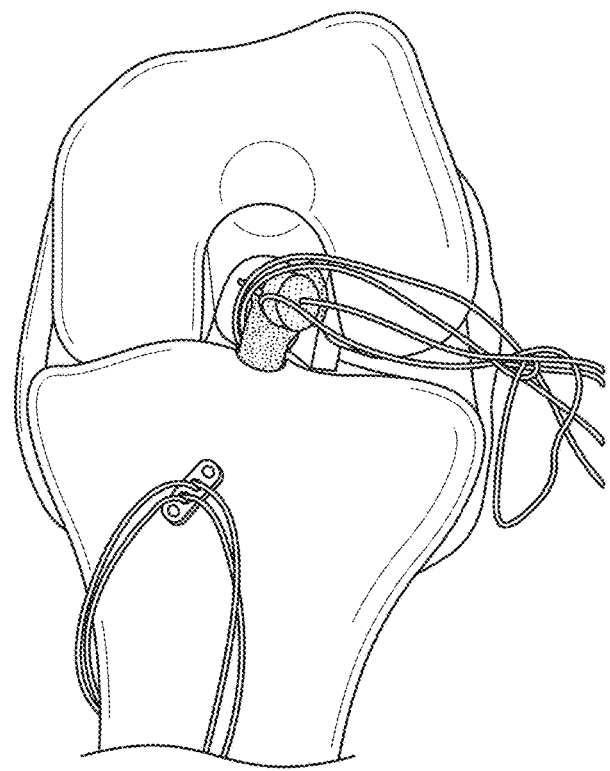
Figure 7K:
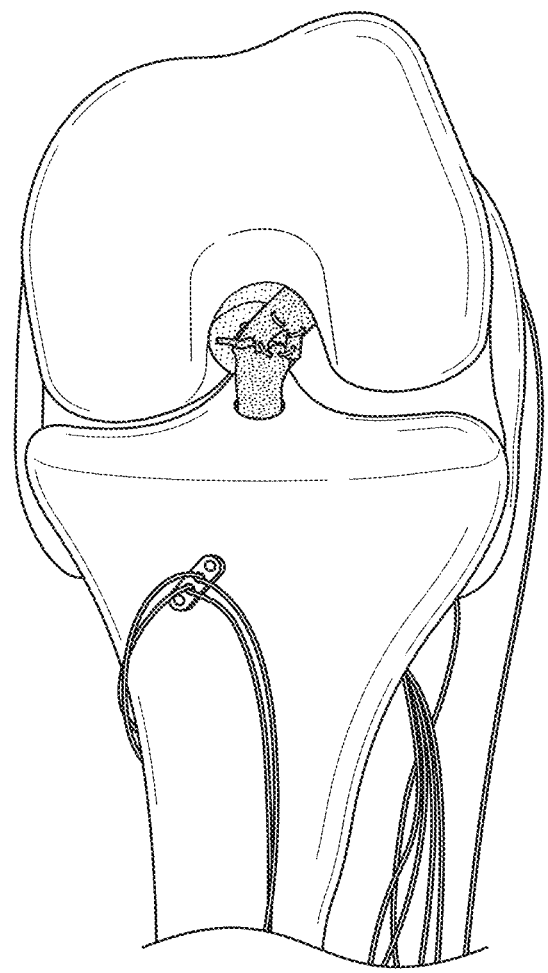

Arthroscopy for meniscal, other pathology may be performed as shown in FIG. 7B. A medial mini-arthrotomy is performed and whip stitch is placed into tibial stump. In FIG. 7C a Tibial Tunnel is drilled. A Tibial Pin is placed adjacent to ACL stump using an aiming device and over-drilled with a reamer that has sufficient diameter to allow for suture passage through the tunnel. In FIG. 7D a guide pin is placed in femoral insertion site of ACL and the proximal cortex is drilled through, followed by overdrilling with a reamer that has sufficient diameter to allow for button passage through the tunnel. In FIG. 7E, a proximal cortical button is assembled with sutures. Vicryl passing loops are placed through outer holes and non-absorbable Core sutures are placed through inner holes. The sutures that have been attached to the ACL tissue are passed thru central holes. In FIG. 7F the cortical button is passed through femoral tunnel and engaged on proximal cortex. Vicryl Passing Sutures are put in outer holes and sutures to ACL whip stitch thru central holes. In FIG. 7G a straight needle is used to thread scaffold onto the Core Sutures. The free ends of Core sutures were passed through tibial tunnel. In FIG. 7H a scaffold is passed up into notch along the Core sutures. The tibial stump is kept anterior to scaffold. Autologous blood (10 cc) is added to the scaffold. In FIG. 7I, the knee was extended and the core sutures were pulled down and tied over a second cortical button. The Tibial stump of ACL remains anterior to scaffold. In FIG. 7J the ACL stump sutures were pulled proximally to pull the ACL into the scaffold. The sutures were tied using an arthroscopic locking knot down onto the proximal femur to secure the ACL in place.

In these examples, a device for repairing a ruptured or torn ligament includes at least two scaffolds, one suture and two anchors, such that the combination of scaffolds are configured for repair is shown. A scaffold that is configured for repair is one that is capable of being inserted into an area requiring repair and promotes regeneration of the ligament. A scaffold of the invention is capable of insertion into a repair site and either forming a connection between the ends of a ruptured ligament, or forming around a torn ligament such that, in either case, the integrity and structure of the ligament is maintained. Regeneration offers several advantages over reconstruction, previously used in ligament repair, including maintenance of the complex insertion sites and fan-shape of the ligament, and preservation of remaining proprioceptive fibers within the ligament substance.

A scaffold (14) may function either as an insoluble or biodegradable regulator of cell function or simply as a delivery vehicle of a supporting structure for cell migration or synthesis. Numerous matrices made of either natural or synthetic components have been investigated for use in ligament repair and reconstruction. Natural matrices are made from processed or reconstituted tissue components (such as collagens and GAGs). Because natural matrices mimic the structures ordinarily responsible for the reciprocal interaction between cells and their environment, they act as cell regulators with minimal modification, giving the cells the ability to remodel an implanted material, which is a prerequisite for regeneration.

Synthetic matrices are made predominantly of polymeric materials. Synthetic matrices offer the advantage of a range of carefully defined chemical compositions and structural arrangements. Some synthetic matrices are not degradable. While the non-degradable matrices may aid in repair, non-degradable matrices are not replaced by remodeling and therefore cannot be used to fully regenerate ligament. It is also undesirable to leave foreign materials permanently in a joint due to the problems associated with the generation of wear particles, thus degradable materials are preferred for work in regeneration. Degradable synthetic scaffolds can be engineered to control the rate of degradation.

A scaffold is preferably made of a compressible, resilient material which has some resistance to degradation by synovial fluid. Synovial fluid as part of normal joint activity, naturally prevents clot formation. This fibrinolytic process would result in the premature degradation of the scaffold and disrupt the healing process of the ligament. The material may be either permanent or biodegradable material, such as polymers and copolymers. The scaffold can be composed, for example, of collagen fibers, collagen gel, foamed rubber, natural material, synthetic materials such as rubber, silicone and plastic, ground and compacted material, perforated material, or a compressible solid material.

A scaffold may be a solid material such that its shape is maintained, or a semi-solid material capable of altering its shape and or size. A scaffold may be made of expandable material allowing it to contract or expand as required. The material can be capable of absorbing plasma, blood, other body fluids, liquid, hydrogel, or other material the scaffold either comes into contact with or is added to the scaffold.

The three-dimensional shaped implants may have shape memory. The shape memory allows the implant to be temporarily deformed, delivered by a minimally invasive method, and resume its preformed three-dimensional shape once placed in the vicinity of the articular tissue.

The scaffolds may vary in shape and size. Shapes include, but are not limited to, beads, spheres, cylinders, squares, rectangles, triangles, ellipsoids, hemispheres, hemi-ellipsoids, domes or similar kinds of shapes. The sizes of the scaffolds vary, and range, for example, from a width of 0.5 to 50 mm, 0.5 to 30 mm, 0.5 to 20 mm, 1 to 50 mm, 1 to 30 mm, 1 to 10 mm, 2 to 50 mm, 2 to 30 mm, 2 to 10 mm, 5 to 50 mm, 5 to 40 mm, 5 to 30 mm, 5 to 20 mm, 5 to 10 mm, 10 to 100 mm, 10 to 50 mm, 10 to 30 mm, 10 to 10 mm, 10 to 20 mm, 10 to 40 mm, or 10 to 15 mm.

A scaffold material can be protein, lyophilized material, or any other suitable material. A protein can be synthetic, bioabsorbable or a naturally occurring protein. A protein includes, but is not limited to, fibrin, hyaluronic acid, elastin, extracellular matrix proteins, or collagen. A scaffold material may be plastic or self-assembling peptides. A scaffold material may incorporate therapeutic proteins including, but not limited to, hormones, cytokines, growth factors, clotting factors, anti-protease proteins (e.g., alpha1-antitrypsin), angiogenic proteins (e.g., vascular endothelial growth factor, fibroblast growth factors), antiangiogenic proteins (e.g., endostatin, angiostatin), and other proteins that are present in the blood, bone morphogenic proteins (BMPs), osteoinductive factor (IFO), fibronectin (FN), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, transforming growth factor (TGF-beta), insulin-like growth factor (IGF-1), platelet derived growth factors (PDGF), fibroblast growth factors (FGF, bFGF, etc.), and periodontal ligament chemotactic factor (PDLGF), for therapeutic purposes. A lyophilized material is one that is capable of swelling when liquid, gel or other fluid is added or comes into contact with it.

Many biological materials are available for making the scaffold, including collagen compositions (either collagen fiber or collagen gel), compositions containing glycosaminoglycan (GAG), hyaluran compositions, and various synthetic compositions. Collagen-glycosaminoglycan (CG) copolymers have been used successfully in the regeneration of dermis and peripheral nerve. Porous natural polymers, fabricated as sponge-like and fibrous scaffolds, have been investigated as implants to facilitate regeneration of selected musculoskeletal tissues including ligaments. A scaffold, such as a sponge scaffold, may also be made from tendon (xenograft, allograft, autograft) or ligament or skin or other connective tissue which could be in the native state or processed to facilitate cell ingrowth or other biologic features.

In aspects of the invention, a scaffold is composed of a sponge or sponge-like material. A sponge scaffold may be absorbable or nonabsorbable. A sponge scaffold may be collagen, elastin, extracellular matrix protein, plastic, or self-assembling peptides. A sponge scaffold may be hydrophillic. A sponge scaffold is capable of compression and expansion as desired. For example, a sponge scaffold may be compressed prior to or during implantation into a repair site. A compressed sponge scaffold allows for the sponge scaffold to expand within the repair site. A sponge may be lyophilized and/or compressed when placed in the repair site and expanded once in place. The expansion of a sponge scaffold may occur after contact with blood or other fluid in the repair site or added to the repair site. A sponge scaffold may be porous. A sponge scaffold may be saturated or coated with a liquid, gel, or hydrogel repair material prior to implantation into a repair site. Coating or saturation of a sponge scaffold may ease implantation into a relatively undefined defect area as well as help to fill a particularly large defect area. A sponge scaffold may be composed of collagen. In a preferred embodiment, a sponge scaffold is treated with hydrogel.

An important subset of natural matrices are those made predominantly from collagen, the main structural component in ligament. Collagen can be of the soluble or the insoluble type. Preferably, the collagen is soluble, e.g., acidic or basic. For example, the collagen can be type I, II, III, IV, V, IX or X. Preferably the collagen is type I. More preferably the collagen is soluble type I collagen. Type I collagen is the predominant component of the extracellular matrix for the human anterior cruciate ligament and provides an example of a choice for the basis of a bioengineered scaffold. Collagen occurs predominantly in a fibrous form, allowing design of materials with very different mechanical properties by altering the volume fraction, fiber orientation, and degree of cross-linking of the collagen. The biologic properties of cell infiltration rate and scaffold degradation may also be altered by varying the pore size, degree of cross-linking, and the use of additional proteins, such as glycosaminoglycans, growth factors, and cytokines. In addition, collagen-based biomaterials can be manufactured from a patient's own skin, thus minimizing the antigenicity of the implant (Ford et al., 105 Laryngoscope 944-948 (1995)).

The collagen is synthetic or naturally derived. Natural sources of collagen may be obtained from animal or human sources. For instance, it may be derived from rat, pig, cow, or human tissue or tissue from any other species. Tendons, ligaments, muscle, fascia, skin, cartilage, tail, or any source of collagenous tissue are useful. The material is then implanted into a subject of the same or different species. The terms "xenogeneic" and "xenograft" refer to cells or tissue which originates with or is derived from a species other than that of the recipient. Alternatively, the collagen may be obtained from autologous cells. For instance, the collagen may be derived from a patient's fibroblasts which have been cultured. The collagen may then be used in that patient or other patients. The terms "autologous" and "autograft" refer to tissue or cells which originate with or are derived from the recipient, whereas the terms "allogeneic" and "allograft" refer to cells and tissue which originate with or are derived from a donor of the same species as the recipient. The collagen may be isolated any time before surgery.

The solubilized collagen may be in a concentration of 1-50 mg/ml in the solution. In some embodiments that concentration of solubilized collagen is greater than 5 mg/ml and less than or equal to 50 mg/ml. In some embodiments that concentration of solubilized collagen is greater than 50 mg/ml and less than or equal to 500 mg/ml. The concentration of collagen may be, for instance, 10, 15, 20, 25, 30, 35, or 40 mg/ml. Such high concentrations of collagen are useful for producing viscosity levels that are desirable for the methods of the invention. Most commercially available collagen solutions are of lower concentrations. Higher concentrations can be made, for instance, using the methods described herein. In other embodiments the solubilized collagen solution has a concentration of 1 mg/ml to less than 5 mg/ml. When such lower concentrations of collagen are used, additional components or steps are taken to increase the viscosity of the material in order to be useful according to the methods of the invention. Examples of viscosity inducing methods or components are described herein.

The solution should be prepared, by varying the collagen content and other components, to provide the desired flow properties of the finished composition. In some embodiments the solution has a collagen viscosity of 1,000 to 200,000 centipoise.

The collagen solution is sterile for in vivo use. The solution may be sterilized and/or components of the solution may be isolated under sterile conditions using sterile techniques to produce a sterile composition. The final desired properties of the composition may be determinative of how the solution is sterilized because some sterilization techniques may affect properties such as viscosity. If certain components of the solution are not to be sterilized, i.e., the collagen isolated from natural sources, the remaining components can be combined and sterilized before addition of the collagen, or each component can be sterilized separately. The solution can then be made by mixing each of the sterilized components with the collagen that has been isolated using sterile techniques under sterile conditions. Sterilization may be accomplished, for instance, by autoclaving at temperatures on the order of about 115° C. to 130° C., preferably about 120° C. to 125° C. for about 30 minutes to 1 hour. Gamma radiation is another method for sterilizing components. Filtration is also possible, as is sterilization with ethylene oxide.

In some embodiments the scaffold is hydrophilic. The hydrophilicity of the scaffold can be assessed, for instance, by the ability of the scaffold to absorb an amount greater than its weight in liquid such as water or blood. In some embodiments the scaffold has a hydrophilicity such that it can absorb at least 2× its weight in blood or other fluid. In other embodiments it can absorb at least 5×, at least 10×, or at least 15× its weight in blood or other fluid. For instance the scaffolds described in the examples absorbs 5× its weight. At least 5 ml of blood or other repair material is added to the 1 g scaffold described in Example 2.

The solubilized collagen solution may contain additional components, such as insoluble collagen, other extracellular matrix proteins (ECM), such as proteoglycans and glycosaminoglycans, fibronectin, laminin, entectin, decorin, lysyl oxidase, crosslinking precursors (reducible and non-reducible), elastin, elastin crosslink precursors, cell components such as, cell membrane proteins, mitochondrial proteins, nuclear proteins, cytosomal proteins, and cell surface receptors, growth Factors, such as, PDGF, TGF, EGF, and VEGF, and hydroxyproline. In some embodiments hydroxyproline may be present in the solution in a concentration of 1 to 3.0 μg/ml, which may be 8 to 9% of the total protein in the collagen solution. In some embodiments, the hydroxyproline is present in a concentration of 0.5 to 4.0 μg/ml in the collagen solution prior to the addition of any buffer. In some embodiments the collagen solution is free of thrombin. "Free of thrombin" as used herein refers to a composition which has less than 1% thrombin. In some embodiments, free of thrombin refers to undetectable levels. In other embodiments it refers to 0% thrombin.

A device of the invention may also include one or more fixation devices. An anchor is a device capable of insertion into a bone such that it forms a stable attachment to the bone. In some instances the fixation device is capable of being removed from the bone if desired. Fixation devices include but are not limited to anchors, staples (12), buttons (14), or a knot (tying the suture over a bony bridge). An anchor may be conical shaped having a sharpened tip at one end and a body having a longitudinal axis. The body of an anchor may increase in diameter along its longitudinal axis. The body of an anchor may include grooves suitable for screwing the anchor into position. For example, the anchor may be screwed into the femur bone. An anchor may include an eyelet at the base of the anchor body through which one or more sutures may be passed. The eyelet may be oval or round and may be of any size suitable to allow one or more sutures to pass through and be held within the eyelet.

A fixation device may be attached to a bone by physical or mechanical methods as known to those of ordinary skill in the art. An anchor includes, but is not limited to, a screw, a barb, a helical anchor, a staple, a clip, a snap, a rivet, or a crimp-type anchor. The body of an anchor may be varied in length. Examples of anchors, include but are not limited to, IN-FAST™ Bone Screw System (Influence, Inc., San Francisco, Calif.), IN-TAC™ Bone Anchor System (Influence, Inc., San Francisco, Calif.), Model 3000 AXYALOOP™ Titanium Bone Anchor (Axya Medical Inc., Beverly, Mass.), OPUS MAGNUM® Anchor with Inserter (Opus Medical, Inc., San Juan Capistrano, Calif.), ANCHRON™, HEXALON™ TRINION™ (all available from Inion Inc., Oklahoma City, Okla.) and TwinFix AB absorbable suture anchor (Smith & Nephew, Inc., Andover, Mass.). Anchors are available commercially from manufacturers such as Influence, Inc., San Francisco, Calif., Axya Medical Inc., Beverly, Mass., Opus Medical, Inc., San Juan Capistrano, Calif., Inion Inc., Oklahoma City, Okla., Arthrex (Naples FL), and Smith & Nephew, Inc., Andover, Mass.

The fixation device may be composed of a non-degradable material, such as metal, for example titanium 316 LVM stainless steel, CoCrMo alloy, or Nitinol alloy, or plastic. The bony fixation device is preferably bioabsorbable such that the subject is capable of breaking down the anchor and absorbing it. Examples of bioabsorbable material include, but are not limited to, MONOCRYL (poliglecaprone 25), PDS II (polydioxanone), surgical gut suture (SGS), gut, coated VICRYL (polyglactin 910, polyglactin 910 braided), human autograft tendon material, collagen fiber, POLYSORB, poly-L-lactic acid (PLLA), polylactic acid (PLA), polysulfone, polylactides (Pla), racemic form of polylactide (D,L-Pla), poly(L-lactide-co-D,L-lactide), 70/30 poly(L-lactide-co-D,L-lactide), polyglycolides (PGa), polyglycolic acid (PGA), polycaprolactone (PCL), polydioxanone (PDS), polyhydroxyacids, and resorbable plate material (see e.g. Orthopedics, October 2002, Vol. 25, No. 10/Supp.). The anchor may be bioabsorbed over a period of time which includes, but is not limited to, days, weeks, months or years.

A suture (12) is preferably bioabsorbable, such that the subject is capable of breaking down the suture and absorbing it, and synthetic such that the suture may not be from a natural source. A suture (12) may be permanent such that the subject is not capable of breaking down the suture and the suture remains in the subject. A suture (12) may be rigid or stiff, or may be stretchy or flexible. A suture (12) may be round in shape and may have a flat cross section. Examples of sutures include, but are not limited to, VICRYL™ polyglactin 910, PANACRYL™ absorbable suture, ETHIBOND® EXCEL polyester suture, PDS® polydioxanone suture and PROLENE® polypropylene suture. Sutures are available commercially from manufacturers such as MITEK PRODUCTS division of ETHICON, INC. of Westwood, Mass. The suture may be as long as the ACL or longer. In an embodiment, the suture length is more than 30" in length. In some embodiments, the suture is long enough to be doubled over and for both ends to be able to traverse the femur and tibia, with sufficient extra length to allow for the suture to have a loop outside the knee where the scaffolds are maintained until the suture is pulled tight (Se FIGS. 3-6, for instance).

A staple is a type of anchor having two arms that are capable of insertion into a bone. In some instances, the arms of the staple fold in on themselves when attached to a bone or in some instances when attached to other tissue. A staple may be composed of metal, for example titanium or stainless steel, plastic, or any biodegradable material. A staple includes but is not limited to linear staples, circular staples, curved staples or straight staples. Staples are available commercially from manufacturers such as Johnson & Johnson Health Care Systems, Inc. Piscataway, N.J., and Ethicon, Inc., Somerville, N.J. A staple may be attached using any staple device known to those of ordinary skill in the art, for example, a hammer and staple setter (staple holder). In some embodiments, a staple may be used to hold the suture securely in position.

A repair site (26) is the area around a ruptured or torn ligament (2) into which a device of the invention may be inserted. A device of the invention may be placed into a repair site (26) area during surgery using techniques known to those of ordinary skill in the art. A scaffold (14) of the invention can either fill the repair site (26) or partially fill the repair site (26). A scaffold (18) can partially fill the repair site (26) when inserted and expand to fill the repair site (26) in the presence of blood, plasma or other fluids either present within the repair site (26) or added into the repair site (26).

A scaffold of the device can be pretreated with a repair material prior to implantation into a subject. The scaffold may be soaked in a repair material prior to or during implantation into a repair site. The repair material may be injected directly into the scaffold prior to or during implantation. The repair material may be injected within a tubular scaffold at the time of repair. Repair material includes, but is not limited to, a gel, for example a hydrogel, a liquid, or collagen. A liquid includes any material capable of forming an aqueous material, a suspension or a solution. A repair material may include additional materials, such as growth factors, antibiotics, insoluble or soluble collagen (in fibrous, gel, sponge or bead form), a cross-linking agent, thrombin, stem cells, a genetically altered fibroblast, platelets, water, plasma, extracellular proteins and a cell media supplement. The additional repair materials may be added to affect cell proliferation, extracellular matrix production, consistency, inhibition of disease or infection, tonicity, cell nutrients until nutritional pathways are formed, and pH of the repair material. All or a portion of these additional materials may be mixed with the repair material before or during implantation, or alternatively, the additional materials may be implanted proximate to the defect area after the repair material is in place.

In certain embodiments, a repair material may include collagen and one or more blood cells, i.e. white blood cells (WBC), platelets, or whole blood). In some embodiments, WBC, platelets, or whole blood are derived from the subject to be treated. In other embodiments, WBC, platelets, or whole blood are derived from a donor that is allogeneic to the subject. In certain embodiments, WBC, platelets, or whole blood may be obtained as platelet rich plasma (PRP). In a non-limiting example, WBC, platelets, or whole blood may be isolated from a subject's blood using techniques known to those of ordinary skill in the art. As an example, a blood sample may be centrifuged at 700 rpm for 20 minutes and the platelet-rich plasma upper layer removed. Platelet density may be determined using a cell count as known to those of ordinary skill in the art. WBCs or whole blood may be obtained using similar techniques known to the skilled artisan. The platelet rich plasma may be mixed with collagen and used as a scaffold. The platelet rich plasma may be mixed with any one or more of the scaffold materials of the invention.

In other embodiments, the repair material is autologous blood. In other embodiments, the repair material is composed of white blood cells, red blood cells, platelets or plasma. In other embodiments, the repair material is composed of monocytes, eosinophils, basophils or neutrophils. In other embodiments, the repair material is composed of autologous blood which has been treated after removal from the patient to increase the presence of a specific type of white blood cell within the repair material. In one embodiment, the blood has been treated to increase the presence of monocytes in the repair material. In other embodiments, the patient has been treated prior to surgery to increase the presence of white blood cells and/or platelets in the circulating blood that is drawn to use for the repair material.

An example of a gel is a hydrogel. A hydrogel is a substance that is formed when an organic polymer (natural or synthetic) is crosslinked via covalent, ionic, or hydrogen bonds to create a three-dimensional open-lattice structure which entraps water molecules to form a gel. A polymer may be crosslinked to form a hydrogel either before or after implantation into a subject. For instance, a hydrogel may be formed in situ, for example, at a repair site. In certain embodiments, a polymer forms a hydrogel within the repair site upon contact with a crosslinking agent. Naturally occurring and synthetic hydrogel forming polymers, polymer mixtures and copolymers may be utilized as hydrogel precursors. See for example, U.S. Pat. No. 5,709,854. In certain embodiments, a hydrogel is a gel and begins setting immediately upon mixture and takes approximately 5 minutes to sufficiently set before closure of the defect and surgery area. Setting time may vary depending on the mixture of gel used and environmental factors.

For instance, certain polymers that can form ionic hydrogels which are malleable may be used to form the hydrogel. For example, a hydrogel can be produced by cross-linking the anionic salt of alginic acid, a carbohydrate polymer isolated from seaweed, with calcium cations, whose strength increases with either increasing concentrations of calcium ions or alginate. Modified alginate derivatives, for example, which have an improved ability to form hydrogels or which are derivatized with hydrophobic, water-labile chains, e.g., oligomers of .epsilon.-caprolactone, may be synthesized. Additionally, polysaccharides which gel by exposure to monovalent cations, including bacterial polysaccharides, such as gellan gum, and plant polysaccharides, such as carrageenans, may be crosslinked to form a hydrogel. Additional examples of materials which can be used to form a hydrogel include polyphosphazines and polyacrylates, which are crosslinked ionically, or block copolymers such as PLURONICS™ (polyoxyalkylene ether) or TETRONICS™ (nonionic polymerized alkylene oxide), polyethylene oxide-polypropylene glycol block copolymers which are crosslinked by temperature or pH, respectively. Other materials include proteins such as fibrin, polymers such as polyvinylpyrrolidone, hyaluronic acid and collagen. Polymers such as polysaccharides that are very viscous liquids or are thixotropic, and form a gel over time by the slow evolution of structure, are also useful.

Another example of a gel is hyaluronic acid. Hyaluronic acid, which forms an injectable gel with a consistency like a hair gel, may be utilized. Modified hyaluronic acid derivatives are particularly useful. Hyaluronic acid is a linear polysaccharide. Many of its biological effects are a consequence of its ability to bind water, in that up to 500 ml of water may associate with 1 gram of hyaluronic acid. Esterification of hyaluronic acid with uncharged organic moieties reduces the aqueous solubility. Complete esterification with organic alcohols such as benzyl renders the hyaluronic acid derivatives virtually insoluble in water, these compounds then being soluble only in certain aprotic solvents. When films of hyaluronic acid are made, the films essentially are gels which hydrate and expand in the presence of water.

A gel may be provided in pharmaceutical acceptable carriers known to those skilled in the art, such as saline or phosphate buffered saline. Such carriers may routinely contain pharmaceutically acceptable concentrations of salt, buffering agents, preservatives, compatible carriers, supplementary immune potentiating agents such as adjuvants and cytokines and optionally other therapeutic agents.

As used herein, the term "pharmaceutically acceptable" means a non-toxic material that does not interfere with the effectiveness of the biological activity of the scaffold material or repair material. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the scaffold material is combined to facilitate the application. The components of the pharmaceutical compositions also are capable of being co-mingled with the device of the present invention, and with each other, in a manner such that there is no interaction which would substantially impair the desired pharmaceutical efficacy.

The devices of the invention may be used in surgical procedures. The following is an example of a surgical procedure which may be performed using the devices and methods of the invention. The affected extremity is prepared and draped in the standard sterile fashion. A tourniquet may be used if indicated. Standard arthroscopy equipment may be used. After diagnostic arthroscopy is performed, and the intra-articular lesion identified and defined, two sutures are fixed to the femur at a location in the intercondylar notch which is not in the native insertion site of the anterior cruciate ligament. The torn anterior cruciate ligament tissue is left in situ and not damaged by drilling though it or placing suture into it. Two or more scaffolds are then sequentially introduced, into the intercondylar notch. The sutures are then both anchored to the tibia to stabilize the knee and hold the two scaffolds in the vicinity of the torn ACL. The arthroscopic portals can be closed and a sterile dressing placed. The post-operative rehabilitation is dependent on the joint affected, the type and size of lesion treated, and the tissue involved.

The device of the invention may be used with arthroscopic equipment. The device of the invention may be used by insertion through an open incision. The scaffold is compressible to allow introduction through arthroscopic portals, incisions and equipment. The scaffold can also be pre-treated in antibiotic solution prior to implantation.

A subject includes, but is not limited to, any mammal, such as human, non-human primate, mouse, rat, dog, cat, horse or cow. In certain embodiments, a subject is a human.

The invention also includes in some aspects kits for repair of ruptured or torn articular tissue such as ligaments. A kit may include more than one scaffolds of the invention and optionally, one or more sutures and bony fixation devices for the femur and tibia. One or more bone fixation devices may be attached to the suture or sutures in the kit. A kit may further include a container that contains a repair material as described herein.

The kit may include one or more containers housing the components of the invention and/or for collecting or storing blood or cells and instructions for use. The kit may be designed to facilitate use of the methods described herein by surgeons and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include a container housing collagen. The collagen may be in the form of a liquid, gel or solid (powder). The collagen may be prepared sterilely and may be packaged and shipped in the form of multiple scaffolds. Alternatively it may be shipped as a single scaffold that can be separated into multiple scaffolds prior to or at the time of use. A second container may have buffer solution premixed prepared sterilely or in the form of salts. Alternatively the kit may include one or more containment devices. The kit may also include instructions for mixing one or more components of the kit and/or isolating and mixing a sample (e.g., blood taken from a subject) and applying to a subject.

The kit may have one or more or all of the components required to draw blood from a patient, process the sample into platelet concentrate or WBCs to make a repair material, and to deliver the repair material to a surgical site. For instance, a kit for withdrawing blood from a patient may include one or more of the items required for such a procedure. For example, typically when an injection is to be made, the patient's skin is cleansed with a disinfecting agent, such as an alcohol wipe; then a second disinfecting agent, such as iodine or Betadine may be applied to the skin; an area is usually isolated with a tourniquet to restrict the blood flow within the artery or vein making the vessel more visible before the needle is inserted, a needle attached to a collection device, such as a vacutainer tube is injected through the patient's skin to withdraw the blood; the needle is then removed and wiped clean; and the puncture site is covered with an absorbent pad until after hemostasis.

The kit may also contain substances designed for administration to a patient prior to the blood being drawn for use as a repair material. For example, the kit may contain a specific dose of a growth factor known to result in increased circulating monocyte concentration so the blood drawn at the time of surgical repair is more favorable for regeneration of the injured tissue.

The accessories included may be specifically designed to allow the practitioner to withdraw blood from the patient. For instance, the accessories may include one or more of the following a tourniquet, a skin penetration instrument, a device for housing blood, a collection tube, disinfecting agents or post-injection bleeding patches.

The skin penetrating instrument for initiation of blood flow may be a conventional device such as a needle. The needle may be single or double ended and may be of any gauge, preferably 21 or 23 gauge. It optionally has a safety sleeve, may be attached to a needle hub, and preferably is used with a conventional tube holder. The needle may also be part of a conventional syringe assembly including barrel and plunger. The needle may be part of a conventional blood collection set in which a penetrating needle having a grasping means, such as wings, is connected via a hub and tubing to a delivery needle for puncture of a septum of an evacuated tube.

The device for housing the blood may be any type of container for receiving the blood sample, such as, for example, a syringe barrel or it may be a device to which the blood sample is transferred following collection, for example a tube. Preferred devices for housing the blood are conventional tubes or vials having a closed end and an open end. Such tubes may have an internal volume of 100 μl to 100 ml. Devices to house the blood after it has been collected include for instance, vials, centrifuge tubes, vortex tubes or any other type of container. The device for receiving the blood may be an evacuated tube in which the open end is covered by a puncturable septum or stopper, such as a vacutainer tube. Evacuated tubes are generally used with a conventional tube holder and blood collection set for collection of multiple larger blood samples, and may contain any of a variety of conventional blood analysis additives, such as anticoagulants. Preferred anticoagulants are citrate and ethylenediaminetetra acetic acid (EDTA).

The plasma, which contains the platelets, may be used together with other components of the blood or it may be separated from the whole blood. Any separation technique can be utilized, for example, sedimentation, centrifugation or filtration. Centrifugation can be carried out at about 500 g for about 20 minutes to obtain platelets. The supernatant, which contains the plasma, can be removed by standard techniques. Filtration can be carried out by passing the whole blood through a suitable filter that separates blood cells from plasma.

Optionally the kits may include disinfecting agents and post-injection bleeding patches. A means for sterilizing the patient's skin in the area of intended puncture, such as a disinfecting agent may be provided. A typical and conventional disinfecting agent is a piece of fabric commonly referred to as a gauze combined with a disinfectant. Some typical disinfecting agents include rubbing alcohol, antibacterial agents, iodine, and Betadine, which may or may not be provided with application pads in individually sealed packets. The post-injection bleeding patch can also vary from a relatively simple gauze pad plus adhesive strips, to a bandage.

When a blood draw is to be made, the practitioner may open the sealed kit; isolate a selected region of the patient's body, such as the lower arm, with the tourniquet to restrict the blood flow within the region and make the blood vessels more visible; clean the injection site with one or more of the sterilizing agents; attach the needle to the collection tube; inject the needle into the patient's blood vessel and collect the blood sample in the tube; withdraws the needle from the skin; and covering the puncture site with an absorbent pad. The blood may then be processed to produce a concentrate of platelets or white blood cells.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag.

The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art.

The kit may also contain any other component needed for the intended purpose of the kit. Thus, other components may be a fabric, such as gauze, for removing the disinfecting agent after the sterilizing step or for covering the puncture wound after the sample is drawn. Other optional components of the kit are disposable gloves, a support for the device for holding blood after the sample is taken, adhesive or other device to maintain the fabric in place over the puncture wound.

The kit may include disposable components supplied sterile in disposable packaging. The kit may also include other components, depending on the specific application, for example, containers, cell media, salts, buffers, reagents, syringes, needles, etc.

EXAMPLES

Example 1: Comparison of the Effects of Multiple Discreet Scaffolds Versus a Single Intact Scaffold on Ligament Repair Methods
Study Design IACUC approvals were obtained prior to initiating the study. Sixteen late adolescent Yucatan mini-pigs underwent ACL transection and were then randomized to bio-enhanced ACL reconstruction with BPTB allograft using a bioactive scaffold(s) and bio-enhanced ACL repair using the same bioactive hydrophilic scaffold(s). The animals within each treatment group were allowed to heal for 12-months, respectively, at which time the hind limbs were harvested.

Preparation of the Extra-Cellular Matrix Scaffold

The bioactive hydrophilic scaffolds (MIACH, Boston Children's Hospital, Boston MA) were manufactured as previously described.[28] A slurry of extracellular matrix proteins was produced by solubilizing bovine connective tissue. The collagen concentration was adjusted to a minimum of 10 mg/ml and lyophilized. For the bio-enhanced ACL reconstruction group, the scaffold was a porous hollow cylinder with an outer diameter of 22 mm, inner diameter of 10 mm, and length of 30 mm.[28] For the bio-enhanced ACL repair group, the scaffolds were a porous cylinder 22 mm in diameter and 30 mm long[15]. All sponges were stored at −20° C. until the day of surgery. At the time of surgery, scaffolds were either implanted either as intact cylinders, or as multiple pieces of the cylinder. When implanted in the joint, the bioactive scaffolds, platelets were added as a repair material.

Surgical Technique: ACL Transection

A medial arthrotomy was created and the fat-pad partially resected to expose the ACL. The ACL was cut between the proximal and middle thirds of the ligament with a scalpel. A Lachman test was performed to verify ACL transection. The knee was then irrigated with 500 cc of normal saline. For those animals assigned to receive no treatment, the incision was closed in layers as previously described.[38]

Surgical Technique: Bio-Enhanced ACL Reconstruction

Following ACL transection, an ACL reconstruction procedure was performed using fresh-frozen bone-patellar tendon-bone allografts harvested from age, weight, and gender matched donor animals as previously described.[15] The entire patellar tendon (~10 mm in width) was used for the soft tissue portion of the graft while the bone plugs were trimmed to 7 mm diameter. Femoral graft fixation was achieved with a 6×20 mm bio-absorbable interference screw (Biosure; Smith & Nephew, Andover, MA). The graft was then manually pre-conditioned in tension twenty times. The cylindrical extracellular matrix based scaffold was threaded onto the graft and positioned to cover the intra-articular soft tissue portion and whether the scaffold was delivered in its intact form or in multiple sections was recorded. The distal bone plug was then seated retrograde into the tibial tunnel and fixed to the tibia using a second 6 mm interference screw and an extracortical tibial button. 3 cc of autologous blood containing platelets were used to saturate the scaffold in situ. The incisions were closed in layers after ten minutes.

Surgical Technique: Bio-Enhanced ACL Repair

Bio-enhanced ACL repair was performed as previously described.[28] In brief, an Endobutton carrying three looped sutures was passed thru a 4 mm femoral tunnel and flipped. Two of the sutures were threaded through the scaffold. The scaffold was maintained outside the knee while the sutures were placed into a predrilled tibial tunnel. The cylindrical scaffold was then slid along the sutures into the notch and note was made if the scaffold was intact at delivery or delivered as multiple transverse sections. The sutures were pulled tight and fixed extracortically over the tibia using a button with the knee in maximum extension (30 degrees). The remaining suture was tied to a Kessler suture of #1 Vicryl (Ethicon, Somerville, NJ) which had been placed in the tibial stump of the ACL. 3 cc of autologous blood containing platelets were used to saturate the scaffold in situ. The incisions were closed in layers after ten minutes.

Following surgery, all animals were housed for four weeks in individualized pens and were then shipped to a farm for long-term porcine care (Coyote Consulting Corporation Inc, Douglas, MA). After 6- and 12-months of healing, the animals were euthanized and the limbs harvested. The knees were immediately frozen at −20° C. until mechanical testing.

Biomechanical Testing

The knees were prepared for biomechanical testing as previously described.[15] The biomechanical testing procedures (i.e., AP knee laxity, structural properties) were performed using a servohydraulic load frame and custom fixtures (MTS Systems Corporation, Eden Prairie, MN).[15] All investigators were blinded to the treatment group during specimen preparation and biomechanical testing. AP knee laxity was measured at 30°, 60°, and 90° of knee flexion by applying fully-reversed, sinusoidal anterior-posterior directed shear loads of ±40N at 0.0833 (1/12) Hz for 12 cycles at each knee angle.[13] The structural properties of the ligaments and grafts were determined using a standardized failure test protocol.[18] Before starting the tensile test, the femur was lowered until the load across the joint surface was +5N of compression. A ramp at 20 mm/min was initiated and the load-displacement data were recorded at 100 Hz.[21] The yield load, failure load, linear stiffness, displacement to 5N (a "slackness" parameter) and the energy to failure were determined from the MTS load-displacement data.

Results

All animals survived to the one year post op time point. There were no infections or incidence of arthrofibrosis. The mean yield load of the group treated with a bio-enhanced repair using an intact longitudinal scaffold was 133N, while that using a scaffold which was delivered in several large sections was 517N and the yield load when the scaffold was delivered in multiple small sections was 880N. The mean maximum loads were 155N, 673N and 956N respectively for the three groups. Linear stiffness was 35N, 142N and 185N respectively for the three groups (intact, few sections, many sections).

Conclusion

This study demonstrated that delivery of the scaffold used for bio-enhanced ACL repair was more effective when performed by delivering the scaffold in multiple pieces rather than as an intact longitudinal structure that coursed the entire distance between the bones or ligament ends.

Example 2 Clinical Studies

Methods

Patients age 18 to 35 with a complete ACL tear who were less than one month from injury and who had at least 50% of the length of the ACL attached to the tibia on their pre-operative MRI were eligible to enroll in the BEAR group. Patients with a complete ACL tear who were within three months of injury were eligible to enroll in the ACL reconstruction group. Only patients determined to benefit from surgical intervention with autograft hamstring tendon graft were considered for this study. Patients were excluded from either group if they had a history of prior surgery on the knee, history of prior infection in the knee, or had risk factors that might adversely affect healing (nicotine/tobacco use, corticosteroids in the past six months, chemotherapy, diabetes, inflammatory arthritis). Patients were excluded if they had a displaced bucket handle tear of the medial meniscus which required repair; all other meniscal injuries were included. Patients were also excluded if they had a full thickness chondral injury, a Grade III MCL injury, a concurrent complete patellar dislocation, or an operative posterolateral corner injury. Two hundred and forty two patients presenting with an ACL injury were screened for participation in this study. Patients were identified as possible candidates if they scheduled an appointment in the Sports Medicine Division with a new knee injury and had an MRI confirming an ACL tear or if they contacted the research coordinator after hearing about the study. Of the 242 patients screened, 22 were enrolled in the study, of which two were excluded before surgery.

Surgical Technique

After the induction of general anesthesia, an examination was performed to verify the positive pivot shift on the injured side and to record the Lachman, range of motion and pivot shift exam results on both knees. A knee arthroscopy was performed and meniscal injuries were treated if present. The tibial aimer (ACUFEX Director Drill Guide, Smith and Nephew, Andover, MA) was used to place a 2.4 mm guide pin up through the tibia in the tibial footprint of the ACL in some patients (in some patients, the holes were drilled near but not within the footprints. This difference did not impact the results.) and then the pin was overdrilled with a 4.5 mm reamer (4.5 mm Endoscopic Drill, Smith and Nephew, Andover, MA). A guide pin was placed in the femoral ACL footprint, drilled up through the femur and then overdrilled with the 4.5 mm reamer. A 2 inch arthrotomy was made at the medial border of the patellar tendon and a whip stitch of #2 Vicryl was placed into the tibial stump of the torn ACL. Two #2 Ethibond sutures were looped through the two center holes of a cortical button (Endobutton, Smith & Nephew, Andover, MA). The #2 Vicryl suture from the tibial stump had the free ends passed through the cortical button and the button carrying the Ethibond and Vicryl sutures was passed through the femoral tunnel and engaged on the lateral femoral cortex. Both of the looped sutures of #2 Ethibond (four matched ends) were passed through the scaffold, and keeping the scaffold out of the joint, the long Ethibond sutures were passed through the tibial tunnel and clamped. The hydrophilic scaffold was then passed up along the sutures into the femoral notch with note being made of whether the scaffold arrived intact or in multiple sections. 10 cc of autologous blood obtained from the antecubital vein was added to the hydrophilic scaffold. The free ends of the Ethibond sutures were pulled tight and tied over a second cortical button on the anterior tibial cortex with the knee in full extension. The remaining pair of suture ends coming through the femur was tied over the femoral cortical button to bring the ACL stump into the scaffold using an arthroscopic surgeon's knot and knot pusher. The arthrotomy was closed in layers.

Figure 8A:
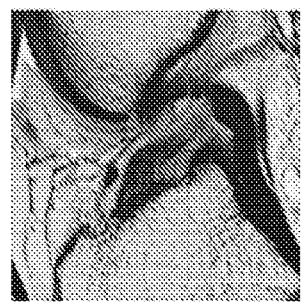
FIGS. 8A-8D: post-operative MRIs from patients having scaffolds delivered in multiple pieces in the notch. The patients had evidence of healing of the ACL.
Figure 8B:
Figure 8C:
Figure 8D:
Figure 9:
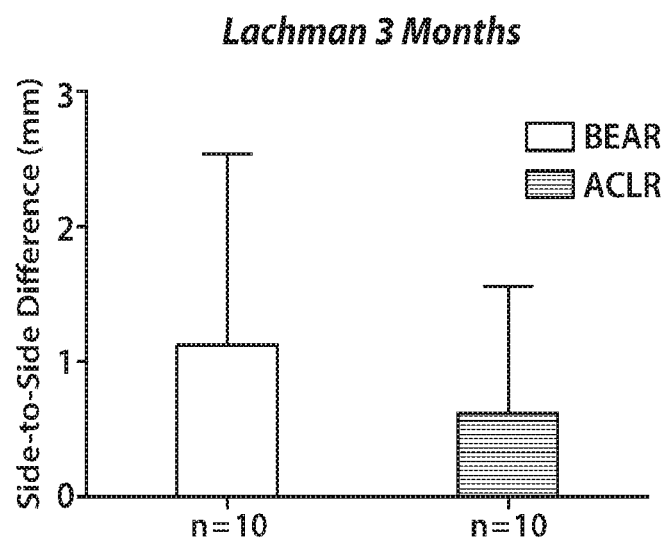
FIG. 9: Graph depicting the results of Lachman Testing at 3 months.
Figure 10:
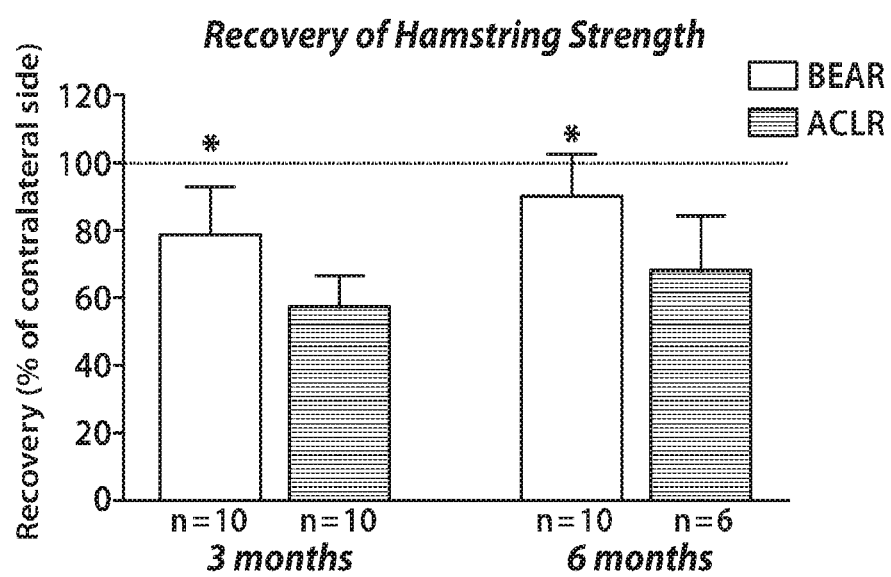
FIG. 10: Graph depicting the results of hamstring strength at 3 and 6 months.

Results:

In all patients, the scaffolds were in multiple pieces after placement in the notch. These patients had evidence of healing of the ACL despite this as noted in their post-operative MRIs (shown in FIG. 8). In FIG. 8A, the torn ACL is visualized. FIG. 8B demonstrates the appearance of the healing ACL at 3 months. The degree of healing is shown at 6 months following surgery in FIG. 8C and at 12 months in FIG. 8D. The results demonstrate good healing of the ACL when the scaffold is delivered in multiple sections, in contrast to the expectation in the art. All knees in the study were stable at the six month post-operative time point, demonstrating effective healing of the injured ACL. The results of Lachman Testing are shown in FIGS. 9 and 10.

Example 3 Large Animal Model Showing Efficacy of Placement of Multiple Scaffolds Around an ACL Graft Methods:

Twenty one Yucatan minipigs underwent ACL transection and reconstruction with a bone-patellar tendon-bone allograft. Seven had no augmentation of the graft placed, seven had a cylindrical graft which was continuous along the entire length of the ACL graft, and seven had sets of multiple scaffolds packed in front of the graft. All animals survived for 12 weeks. Biomechanical testing of the ACL strength were performed at that time point.

Results:

The AP laxity values for the knees treated with the sets of multiple scaffolds packed in front of the graft were lower than that of the untreated ACLs and that of the ACLs treated with the continuous scaffold (at 30 degrees, the values were 3.3+/−1.7 mm, 8.1+/−3 mm and 7+/−3 mm respectively, at 60 degrees, the values were 9+/−1 mm, 13+/−2.4 mm and 11+/−3 mm respectively and at 90 degrees, the values were 8.4+/−1 mm, 13.2+/−2.6 mm and 13.0+/−3 mm respectively). The p value for comparisons of standard ACL reconstruction vs the fragmented group were p=0.00 for all three angles tested and vs the continuous scaffold were p=0.01 for the testing at 30 degrees, p=0.07 at 60 degrees and p=0.00 at 90 degrees.

The displacement to 5N on mechanical testing was also significantly better in the sets of multiple scaffolds group when tested against ACL reconstruction (p=0.00) and continuous scaffold reconstruction (p=0.06).

Thus, use of the sets of multiple scaffolds resulted in less abnormal knee laxity and better healing when used to enhance ACL surgery, quite surprisingly, in contrast to a single scaffold.

Example 4: Clinical Studies of Scaffold-Enhanced Repair with Blood Cells

Patients age 13 to 35 with a complete ACL tear who were less than one month from injury and who had at least 50% of the length of the ACL attached to the tibia on their pre-operative MRI were recruited for a randomized control trial of ACL repair using indirect fixation of the sutures to femur and tibia and set of multiple scaffolds (from scaffold which was noted to be in multiple pieces) prior to wound closure.

Surgical Technique

After the induction of general anesthesia, an examination was performed to verify the positive pivot shift on the injured side and to record the Lachman, range of motion and pivot shift exam results on both knees. A knee arthroscopy was performed and meniscal injuries were treated if present. The tibial aimer (ACUFEX Director Drill Guide, Smith and Nephew, Andover, MA) was used to place a 2.4 mm guide pin up through the tibia in the tibial footprint of the ACL in some patients (in some patients, the holes were drilled near but not within the footprints. This difference did not impact the results.) and then the pin was overdrilled with a 4.5 mm reamer (4.5 mm Endoscopic Drill, Smith and Nephew, Andover, MA). A guide pin was placed in the femoral ACL footprint, drilled up through the femur and then overdrilled with the 4.5 mm reamer. A 2 inch arthrotomy was made at the medial border of the patellar tendon and a whip stitch of #2 Vicryl was placed into the tibial stump of the torn ACL. Two #2 Ethibond sutures were looped through the two center holes of a cortical button (Endobutton, Smith & Nephew, Andover, MA). The #2 Vicryl suture from the tibial stump had the free ends passed through the cortical button and the button carrying the Ethibond and Vicryl sutures was passed through the femoral tunnel and engaged on the lateral femoral cortex. Both of the looped sutures of #2 Ethibond (four matched ends) were passed through the scaffold, and keeping the scaffold out of the joint, the long Ethibond sutures were passed through the tibial tunnel and clamped. The scaffold was then passed up along the sutures into the femoral notch with note being made of whether the scaffold arrived intact or in multiple sections. 10 cc of autologous blood obtained from the antecubital vein was added to the scaffold. The free ends of the Ethibond sutures were pulled tight and tied over a second cortical button on the anterior tibial cortex with the knee in full extension. The remaining pair of suture ends coming through the femur was tied over the femoral cortical button to bring the ACL stump into the scaffold using an arthroscopic surgeon's knot and knot pusher. The arthrotomy was closed in layers. A complete blood count was obtained from the autologous blood added to the scaffold in surgery.

Figure 13:
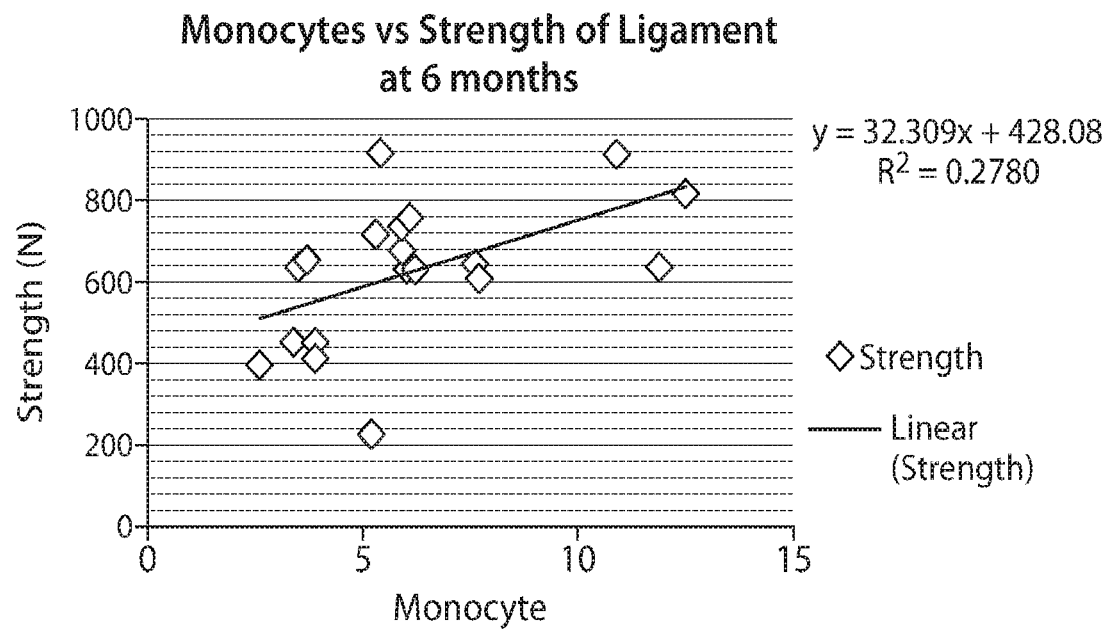
FIG. 13 is a graph depicting the effect of the number of monocytes on strength of ligament at 6 months in a clinical trial of ACL repair using multiple scaffolds.
Figure 14:
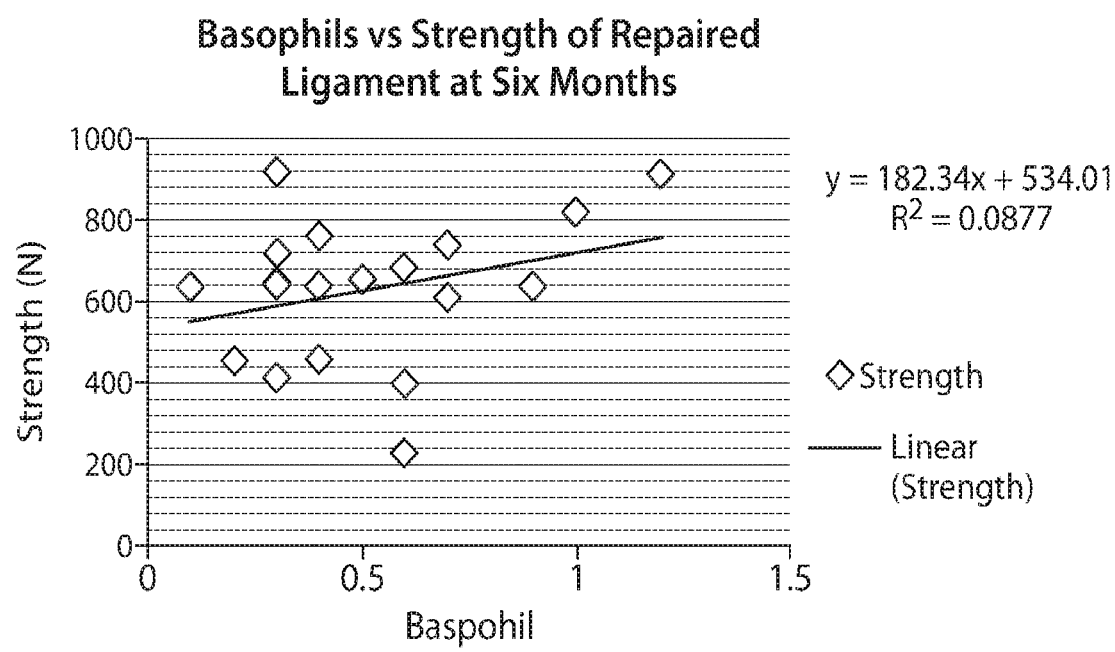
FIG. 14 is a graph depicting the effect of the number of basophils on strength of ligament at 6 months in a clinical trial of ACL repair using multiple scaffolds.
Figure 15:
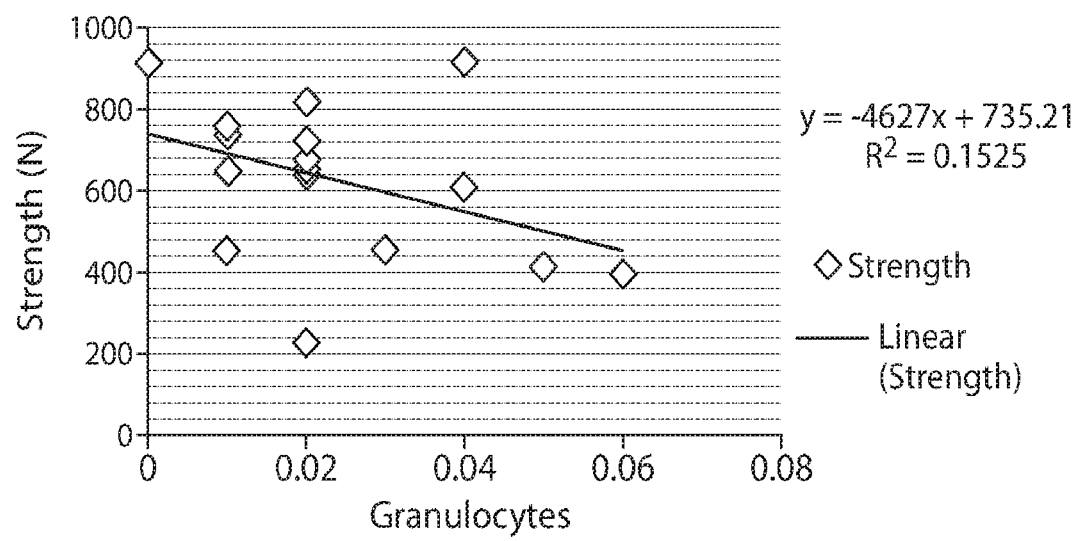
FIG. 15 is a graph depicting the effect of the number of granulocytes on strength of ligament at 6 months in a clinical trial of ACL repair using multiple scaffolds.
Figure 16:
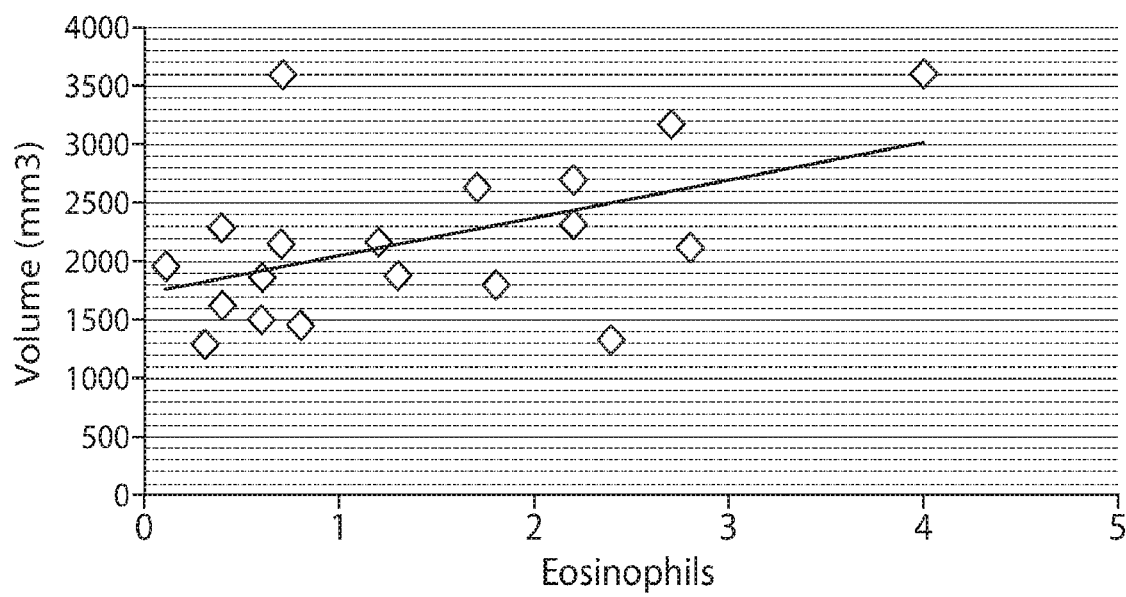
FIG. 16 is a graph depicting eosilophils based on a healing volume in a clinical trial of ACL repair using multiple scaffolds.

Results:

In all patients, the scaffolds were in multiple pieces after placement in the notch. The results demonstrate good healing of the ACL when the scaffold is delivered in multiple sections, in contrast to the expectation in the art. All knees in the study were stable at the six month post-operative time point, demonstrating effective healing of the injured ACL. A noninvasive measure of ligament strength was performed. The number of monocytes in the repair material added to the fragmented scaffold significantly improved the predicted strength of the repair (FIG. 13), as did the number of basophils (FIG. 14). A greater number of granulocytes (FIG. 15); however, resulted in lower strength of the healing ligament. A higher number of eosinophils (FIG. 16) in the repair material was associated with a larger healing ligament volume.

EQUIVALENTS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A device for ligament or tendon repair comprising:
a fixation device capable of forming a stable attachment to a first bone;
a suture having a length, the suture being attachable to a ruptured end of a ligament or tendon, wherein the ruptured end of the ligament or tendon is configured to be connected to a second bone;
multiple distinct biodegradable collagen scaffolds positioned along the length of the suture, the multiple distinct collagen scaffolds each having a first end, a second end opposite the first end, a width, a length that extends from the first end to the second end, where the length is longer than the width, and a collagen concentration of greater than 400 mg/mL, wherein the scaffolds are configured to be positioned at a ruptured end into the gap between the ruptured ligament or tendon and the first bone, and wherein the fixation device is attached only indirectly to the scaffold, the suture extends through the multiple distinct collagen scaffolds along the lengths of the scaffolds and is slidable along the scaffolds, and the multiple distinct collagen scaffolds are configured to regulate cell function at a target site.

2. The device of claim 1, wherein the scaffolds are beads.

3. The device of claim 1, wherein the device for ligament or tendon repair comprises 2-30 scaffolds.

4. A kit, comprising the device of claim 1 and further comprising instructions for surgical repair of a ligament or tendon using the device.

5. The device of claim 1, wherein the scaffolds have a total surface area that is greater than a single scaffold used to repair a ligament or tendon injury.

6. The device of claim 1, wherein the first containment device and the second containment device are sutures and the first scaffold is threaded and slidable along the length of the first suture and the second scaffold is threaded and slidable along the length of the second suture.

7. The device of claim 1, wherein the scaffolds are beads.

8. The device of claim 1, wherein the device for ligament or tendon repair comprises 2-30 scaffolds.

9. A device for ligament or tendon repair comprising:
a set of distinct biodegradable scaffolds comprising 2-30 scaffolds, each scaffold having a collagen concentration of greater than 400 mg/mL, a length of 1-20 mm, a width that is less than 50 mm, and a volume that is less than 100 mL, and each scaffold being capable of absorbing at least 5 mL of blood, wherein the scaffold is configured to be positioned at a ruptured end into the gap between the ruptured ligament or tendon and a bone;
at least one fixation device configured to be secured to the bone; and
a suture threaded along the length of each scaffold of the set of distinct biodegradable scaffolds to position the scaffold between the ruptured end of the ligament or tendon and the bone.

10. The device of claim 9, wherein the scaffolds are compressible expandable scaffolds.

11. The device of claim 9, wherein the scaffolds are collagen sponges.

12. The device of claim 11, wherein the collagen sponges comprise type I soluble collagen.

13. The device of claim 11, wherein the collagen sponges comprise type I soluble collagen and wherein the collagen sponges are prepared from a solution of solubilized collagen in a concentration of less than or equal to 500 mg/ml.

14. The device of claim 9, wherein the scaffolds are hydrophilic.

15. The device of claim 9, wherein each of the scaffolds in the set are the same.

16. The device of claim 9, wherein at least one of the scaffolds in the set is different from the other scaffolds in the set.

17. The device of claim 16, wherein the at least one different scaffold has a different size than the other scaffolds.

18. The device of claim 17, wherein the at least one different scaffold is larger than the other scaffolds.

19. The device of claim 17, wherein the at least one different scaffold is smaller than the other scaffolds.

20. The device of claim 17, wherein the at least one different scaffold is shaped as a sphere.

21. The device of claim 17, wherein the at least one different scaffold is shaped as a cylinder.

22. The device of claim 17, wherein the at least one different scaffold is larger than the other scaffolds.

23. The device of claim 16, wherein the at least one different scaffold has a different shape than the other scaffolds.

24. The device of claim 16, wherein the at least one different scaffold is comprised of a different biodegradable polymer than the other scaffolds.

25. The device of claim 16, wherein the at least one different scaffold has a different size than the other scaffolds.

26. A kit, comprising the device of claim 9 and further comprising one or more containers to house the set of distinct biodegradable scaffolds, and instructions for surgical repair of a ligament or tendon using the device.

27. The kit of claim 26, further comprising a containment device housed in one or more of the containers.

28. The kit of claim 27, wherein the containment device is a suture.

29. The kit of claim 28, wherein the scaffolds are threaded onto the suture.

30. The device of claim 9, wherein the scaffolds are collagen sponges.

31. The device of claim 9, wherein the scaffolds are hydrophilic.

32. A device for ligament or tendon repair comprising:

a suture having a first end and a second end, the second end being attachable to a ruptured end of a ligament or tendon connected to a bone;

a set of multiple distinct biodegradable scaffolds having resistance to degradation by synovial fluid and configured to regulate cell function at a target site, the set of multiple distinct biodegradable scaffolds having:

a first scaffold having a collagen concentration of greater than 400 mg/mL and less than or equal to 500 mg/mL, a length of 1-20 mm, a width of at least 0.5 mm, and a volume of at least 1.0 mL, and positioned along the length of the suture at a ruptured end into the gap between the ruptured ligament or tendon and a bone; and a second scaffold having a collagen concentration of greater than 400 mg/ml and less than or equal to 500 mg/mL, a length of 1-20 mm, a width of at least 0.5 mm, and a volume of at least 1.0 mL, and positioned along the length of the suture at a ruptured end into the gap between the ruptured ligament or tendon and a bone.

* * * * *